US005763284A

United States Patent [19]

Tal et al.

[11] Patent Number: 5,763,284

[45] Date of Patent: Jun. 9, 1998

[54] METHODS FOR PEPTIDE SYNTHESIS AND PURIFICATION

[75] Inventors: Rony Tal, Coral Springs; Hing C. Wong, Ft. Lauderdale; Clayton Casipit, Hialeah; Pierre-Andre Chavaillaz, Cooper City; Vaughan Wittman, Ft. Lauderdale, all of Fla.

[73] Assignee: Dade International Inc., Deerfield, Ill.

[21] Appl. No.: 428,733

[22] Filed: Apr. 25, 1995

Related U.S. Application Data

[63] Continuation-in-part of Ser. No. 235,178, Apr. 29, 1994.

[51] Int. Cl.[6] ........................ G01N 33/53; G01N 33/536; G01N 33/68; C12N 15/62

[52] U.S. Cl. ........................ 436/501; 436/536; 435/69.7; 435/252.3; 435/320.1; 424/193.1; 514/2; 536/23.4

[58] Field of Search ................................ 435/69.7, 252.3, 435/252.33, 320.1, 7.2; 424/185, 191.3; 530/350; 536/23.4; 436/501, 536; 514/2

[56] References Cited

U.S. PATENT DOCUMENTS

| | | | |
|---|---|---|---|
| 4,952,508 | 8/1990 | Chang et al. | 435/252.3 |
| 5,215,896 | 6/1993 | Keck et al. | 435/69.7 |
| 5,258,502 | 11/1993 | Kuranda | 530/350 |

FOREIGN PATENT DOCUMENTS

| | | |
|---|---|---|
| 0244147 | 4/1987 | European Pat. Off. . |
| 0 244 147 | 11/1987 | European Pat. Off. . |
| 63-071178 | 3/1988 | Japan . |
| 2-100685 | 4/1990 | Japan . |
| 92-06211 | 4/1992 | WIPO . |
| 94-10308 | 5/1994 | WIPO . |

OTHER PUBLICATIONS

P. Schatz, *Biotechnology*, 11:1138–1143 (1993).

D. Sherratt et al., *Journal of General Microbiology*, 76:217–230 (1973).

D. Dubnau et al., *J. General Microbiology*, 41:7–21 (1965).

T. Himeno et al., *Journal of Bacteriology*, 168(3):1128–1132 (1986).

V. Wittman et al., *Journal of Bacteriology*, 170(7):3206–3212 (1988).

Smith, et al., *Gene*, 67:31–40; Method and Vector Organism for Controlled Accumulation of the Cloned Heterologous Gene Products in Bacillus Subtitlis (1988).

Imanaka, T., et al., 1981, Journal of Bacteriology, 147(3):776–786.

Imanaka, T., et al., 1992, Journal of Bacteriology, 174(4):1423–1425.

Imanaka, T., et al., 1993, Journal of Fermentation and Bioengineering 76(1):1–6.

Wong, A.C., et al., 1990, in *Genetics and Biotechnology Bacelli*, vol. 3, Zukowski, et al., Eds., pp. 115–122.

Hiramatsu, K., et al., 1992, FEBS Letters, 298(2–3):133–136.

Wittman, V., et al., 1993, Journal of Bacteriology, 175(22):7383–7390.

*Primary Examiner*—Charles L. Patterson, Jr.
*Assistant Examiner*—William W. Moore
*Attorney, Agent, or Firm*—Peter F. Corless

[57] ABSTRACT

The present invention provides novel methods for the synthesis and isolation and purification of a peptide of interest (target peptide). In particular, the invention relates to peptide synthesis, isolation and purification methods that comprise use of penI fusion polypeptides and related gene fusion constructs that encode such polypeptides.

24 Claims, 7 Drawing Sheets

| Immunization | | Titer on F2 | Titer on F1.2-C9 KLH | Titer on F1.2-C9 Ova |
|---|---|---|---|---|
| F1.2-C9 PenI #1 | | | | |
| | Mouse #1 | 1:12,800 | 1:3200 | N.D. |
| | Mouse #2 | 1:12,800 | 1:3200 | N.D. |
| | Mouse #3 | 1:6400 | 1:1600 | N.D. |
| | Mouse #4 | 1:3200 | 1:800 | N.D. |
| | Mouse #5 | >or = 1:12,800 | >or = 1:25,600 | N.D. |
| | Mouse #6 | 1:3200 | 1:800 | N.D. |
| | Mouse #7 | 1:6400 | 1:1600 | N.D. |
| | Mouse #8 | >or = 1:12,800 | 1:12,800 | N.D. |
| | Mouse #9 | 1:6400 | 1:1600 | |
| F1.2-C9 KLH #3 | | | | |
| | Mouse #1 | 1:800 | N.D. | 1:800 |
| | Mouse #2 | 1:6400 | N.D. | 1:3200 |
| | Mouse #3 | >or = 1:12,800 | N.D. | >or = 1:25,600 |
| | Mouse #4 | 1:3200 | N.D. | 1:1600 |
| Controls | | | | |
| F1.2-C9 Ova #2 Mouse #2 | | 1:12,800 | 1:800 | N.D. |
| F1.2-C9 KLH #2 Mouse #2 | | >or = 1:12,800 | N.D. | 1:6400 |
| TA1 Monoclonal Antibody (Conc.= 5.7 mg/ml IgG2a) | | >or = 1:256,000 (22.3 ng/ml) | >or = 1:256,000 (22.3 ng/ml) | 1:32,000 (178.4 ng/ml) |

Hind III
AAG CTT ATG AAA AAA ATA CCT CAA ATC TCT GAT GCG GAA TTA GAA GTG ATG AAA GTC ATC TGG AAG CAT TCT TCG
K L M K K I P Q I S D A E L E V M K V I W K H S S ATC AAT ACC AAT GAG GTA ATT AAA GAG TTA TCC AAA ACC AGT ACA TGG AGC CCT AAA ACC ATC CAA ACC ATG CTG
I N T N E V I K E L S K T S T W S P K T I Q T M L CTG CGC CTC ATT AAA AAA GGC GCT TTA AAC CAC CAT AAA GAA GGA CGG GTT TTC GTT TAC ACA CCA AAT ATA GAC
L R L I K K G A L N H H K E G R V F V Y T P N I D GAA AGT GAT TAT ATA GAG GTT AAG AGT CAC AGT TTT TTA AAC CGG TTT TAC AAT GGA ACT CTT AAT TCG ATG GTA
E S D Y I E V K S H S F L N R F Y N G T L N S M V TTA AAC TTT TTG GAG AAT GAT CAG CTG TCA GGT GAA GAA ATT AAT GAA TTG TAT CAA ATA TTA GAA GAA CAT AAG
L N F L E N D Q L S G E E I N E L Y Q I L E E H K NcoI
AAC AGA AAG AAG GAA CCA TGG GAC TCT GAC CGT GCA ATC GAA GGT CGT TGA G GGATCC
N R K K E P W D S D R A I E G R *
BamHI <u>tFP010</u> GCA TCT GAC CGT GCA ATC GAA GGT CGT TGA
A S D R A I E G R *

<u>tFP011</u> GAC GCT GAC CGT GCA ATC GAA GGT CGT TGA
D A D R A I E G R *

<u>tFP012</u> GAC TCT GCA CGT GCA ATC GAA GGT CGT TGA
D S A R A I E G R *

<u>tFP013</u> GAC TCT GAC GCT GCA ATC GAA GGT CGT TGA
D S D A A I E G R *

<u>tFP014</u> GAC TCT GAC CGT TCC ATC GAA GGT CGT TGA
D S D R S I E G R *

<u>tFP015</u> GAC TCT GAC CGT GCA GCT GAA GGT CGT TGA
D S D R A A E G R *

<u>tFP016</u> GAC TCT GAC CGT GCA ATC GCT GGT CGT TGA
D S D R A I A G R *

<u>tFP017</u> GAC TCT GAC CGT GCA ATC GAA GCA CGT TGA
D S D R A I E A R *

<u>tFP018</u> GAC TCT GAC CGT GCA ATC GAA GGC GCA TGA
D S D R A I E G A *

FIG. 2

| Immunization Group | Date of Injection | Number of Mice | Dose | Route |
|---|---|---|---|---|
| F1.2 C9 KLH #3 | | | | |
| Sensitization | Day 1 | 4 | 56 ug/CFA | I.p. |
| First Boost | Day 70 | 4 | 37 ug/IFA | subcut. |
| Second Boost | Day 101 | 4 | 42 ug/IFA | subcut. |
| F1.2-C9 PEN1 #1 | | | | |
| Sensitization | Day 1 | 10 | 50 ug/CFA | I.p. |
| First Boost | Day 32 | 9 | 38 ug/IFA | subcut. |

FIG. 6

| Immunization | Titer on F2 | Titer on F1,2-C9 KLH | Titer on F1,2-C9 Ova |
|---|---|---|---|
| F1,2-C9 PenI #1 | | | |
| Mouse #1 | 1:12,800 | 1:3200 | N.D. |
| Mouse #2 | 1:12,800 | 1:3200 | N.D. |
| Mouse #3 | 1:6400 | 1:1600 | N.D. |
| Mouse #4 | 1:3200 | 1:800 | N.D. |
| Mouse #5 | >or = 1:12,800 | >or = 1:25,600 | N.D. |
| Mouse #6 | 1:3200 | 1:800 | N.D. |
| Mouse #7 | 1:6400 | 1:1600 | N.D. |
| Mouse #8 | >or = 1:12,800 | 1:12,800 | N.D. |
| Mouse #9 | 1:6400 | 1:1600 | |
| F1,2-C9 KLH #3 | | | |
| Mouse #1 | 1:800 | N.D. | 1:800 |
| Mouse #2 | 1:6400 | N.D. | 1:3200 |
| Mouse #3 | >or = 1:12,800 | N.D. | >or = 1:25,600 |
| Mouse #4 | 1:3200 | N.D. | 1:1600 |
| Controls | | | |
| F1,2-C9 Ova #2 Mouse #2 | 1:12,800 | 1:800 | N.D. |
| F1,2-C9 KLH #2 Mouse #2 | >or = 1:12,800 | N.D. | 1:6400 |
| TA1 Monoclonal Antibody (Conc.= 5.7 mg/ml IgG2a) | >or = 1:256,000 (22.3 ng/ml) | >or = 1:256,000 (22.3 ng/ml) | 1:32,000 (178.4 ng/ml) |

FIG. 7

METHODS FOR PEPTIDE SYNTHESIS AND PURIFICATION

This application is a continuation-in-part of application U.S. Ser. No. 08/235,178, filed Apr. 29, 1994, which application is incorporated herein by reference.

BACKGROUND OF THE INVENTION

1. Field of the Invention

The present invention relates to a novel method for synthesis, isolation and purification of peptides. More particularly, the invention relates to penI fusion polypeptides, peptide synthesis, isolation and purification methods that comprise use of penI fusion polypeptides, and related gene fusion constructs that code for such penI fusion polypeptides.

2. Background

Recombinant DNA methods are employed to produce a variety of peptides. Recombinant DNA technology includes expression of a gene, either synthesized or isolated, to produce a peptide of interest. In brief, a desired DNA sequence is ligated into a cloning vector such as a plasmid. A host cell such as *E. coli*, is transformed with the cloning vector and the transformed host is then cultivated under conditions suitable for expression of the peptide coded for by the DNA sequence. The thus produced proteins are then isolated from the culture medium and typically must be purified. For example, the expressed peptide is often secreted by the host cells into the culture medium and the peptide must be separated from the culture medium and other material in that medium such as cell waste products, other peptides, etc.

Peptides also may be produced by chemical synthesis techniques, although in many applications a chemical synthetic approach may be less preferred than a recombinant procedure. For example, peptides greater than about forty or fifty amino acids in length often cannot be chemically synthesized in acceptable yields. Further, purification of relatively large chemically synthesized peptides often can be more burdensome than corresponding recombinant peptides.

A number of methods have been reported to isolate and purify proteins, including peptides produced by chemical synthesis or recombinant DNA techniques. For example, known purification methods include centrifugation, column chromatography and electrophoresis. While these methods can produce a purified peptide, they each require one or more additional and often burdensome purification steps after initial purification of the peptide. Moreover, in many current isolation and purification procedures, a significant amount of the crude peptide is lost during the procedure resulting in reduced yields.

In certain prior peptide isolation and purification schemes, hybrid or fusion polypeptides have been employed. These approaches have generally provided construction of a gene fusion that codes for a polypeptide that contains a peptide of interest linked to a peptide that exhibits specific binding characteristics not exhibited by the peptide of interest.

These prior fusion peptide methods present notable shortcomings including low yields of purified protein as well as multiple step isolation and purification protocols. For example, in EP 0244147 a fusion polypeptide is described that contains a beta-galactosidase moiety linked to a desired peptide through a renin cleavage site. To isolate and purify the desired peptide, the fusion polypeptide is adsorbed to an affinity matrix and, after eluting to remove other proteins, renin is added to the bound complex to cleave the fusion polypeptide and release the peptide of interest while the beta-galactosidase remains bound to the matrix. In a still further step the isolated peptide is purified by anion exchange chromatography.

It thus would be desirable to have new and simple methods for the synthesis and purification of peptides, particularly peptides produced by recombinant means. It would be further desirable to have such new methods that enable convenient isolation and purification of a desired peptide in a single step, particularly without significant reduction in yields.

SUMMARY OF THE INVENTION

The present invention provides a method for synthesis and purification of essentially any peptide (referred to herein as the "target peptide") by formation of a fusion polypeptide comprising the target peptide linked to the penI repressor protein, or the precipitation effective portion of the penI repressor protein.

The penI repressor protein is produced by *Bacillus licheniformis* and negatively controls the synthesis of the inducible enzyme penicillinase (penP). See Dubnau, et al., *J. Gen. Microbiol.*, 41:7–21 (1965); Sheratt, et al., *J. Gen. Microbiol.*, 76:217–230 (1973). The sequence of the penI gene, expression of that gene in *E. coli* and purification of the penI protein have been reported. See T. Himeno, et al., *J. Bacteriol.*, 68:1128–1132 (1986); Wittman, et al., *J. Bacteriol.*, 170:3206–3212 (1988).

It has been found that penI fusion polypeptides of the invention can be purified in a single step after expression of the polypeptide in a transformed host cell. Specifically, it has been found that a penI fusion polypeptide produced in accordance with the invention can be selectively precipitated from a solution by reducing the solution's ionic strength. It has thus been found that crude cell extract or supernatant thereof that contains the fusion polypeptide can be contacted with a low ionic strength aqueous solution to thereby precipitate the polypeptide. Typically a solution having a salt concentration of about 200 mM or less will be sufficient to precipitate the fusion polypeptide. A preferred means of precipitation is dialysis of a solution of the fusion peptide against a low ionic strength solution. Further purification of the precipitated material such as by reprecipitation and/or chromatography can be carried out if desired, but is not necessary for many applications.

The fusion polypeptide of the invention preferably also includes a linking sequence interposed between the penI protein and target peptide. Further preferred is where the linking peptide sequence can be recognized and cleaved by an appropriate cleavage agent, preferably without deleteriously affecting the target protein. Typically the linking sequence will include an enzyme cleavage site such as a factor Xa site.

The invention further includes DNA fusion vectors that comprise a nucleotide sequence that encodes the penI peptide, or precipitation effective portion thereof, and a sequence coding for the target peptide. Preferably the vector also includes a nucleotide sequence coding for a linking segment that is interposed between the penI protein and target peptide. The linking segment preferably can be recognized and cleaved by an appropriate cleavage agent, preferably without deleteriously affecting the target peptide.

The invention also includes fusion polypeptides that comprise the penI peptide or a precipitation effective portion thereof fused to the amino acid sequence of the target peptide. Preferably the polypeptide further includes a linking segment that is interposed between the penI protein and target peptide. As mentioned above, the linking segment preferably includes an amino acid sequence that can be recognized and cleaved by an appropriate cleavage agent without deleteriously affecting the target peptide.

The invention also includes methods using penI as an antigenic carrier. Use of a fusion polypeptide of the invention for immunization with the penI portion acting as an antigenic carrier is significantly more convenient than prior immunization methods.

The invention also includes methods for fine epitope mapping of selected peptides and preparation and use of random peptide libraries.

The invention also provides methods using a fusion polypeptide of the invention as an antigen(s) in in vitro systems, particularly for use in various assays, e.g., to evaluate if a particular target peptide can stimulate or suppress an immune response as may indicated by inducing or enhancing proliferation of T cells, or alternatively inhibiting T cell proliferation. Such assays will be useful, among other things, to identify target peptides that can be employed to treat a mammal such as a human that suffers from or is susceptible to an autoimmune disorder such as multiple sclerosis, insulin-dependent diabestes mellitus, rheumatoid arthritis and the like, or for treatment of such mammals suffering from or potentially likely to suffer from an undesired immune response e.g., subjects suffering from chronic allergies or patients undergoing some type of transplant surgery such as transplant of heart, kidney, skin or other organs. Such assays will also be useful to identify peptides that invoke an immune response and that may have use in vaccine applications, e.g. to vaccinate a mammal such as a human against an infectious agent or a targeted disorder such as cancer, particularly a melanoma cancer, or other disorder such as malaria.

Moreover, fusion polypeptides of the invention can be prepared quite efficiently in good yields, especially relative to yields for obtaining the target peptide itself (i.e., not linked to the penI protein or precipitation effective portion thereof). Accordingly, the invention provides an efficient method for evaluating biological activity or other properties of a variety of target peptides by producing the peptide(s) as a component of a fusion polypeptide of the invention. Additionally, in the case of at least certain target peptides, it is believed that the ability of a peptide to induce or enhance T cell proliferation in vitro or in vivo may be increased when the peptide is fused to a penI protein or effective portion thereof in accordance with the invention. See, for instance, the results of Example 11 which follows.

Other aspects of the invention are discussed infra.

As used herein, the term "a precipitation effective portion of the penI protein" is defined to mean a portion of the penI protein that when fused to a target peptide will result in precipitation of the fused polypeptide upon contact (such as by method disclosed in Example 1, infra) with an aqueous solution having a low ionic strength. Thus a precipitation effective portion of the penI protein can be readily identified experimentally by those having no more than ordinary skill in the art, i.e., a gene construct can be prepared that contains a DNA sequence coding for a portion of the penI protein and a DNA sequence coding for a target peptide, that gene construct expressed, and the expressed polypeptide contacted with a low ionic strength solution as disclosed herein to determine if precipitation of the fused polypeptide occurs. Typically, at least about 50 percent of the amino acid sequence of a precipitation effective portion of the penI protein will be the same as the sequence of the penI protein, more typically at least about 70 percent of the amino acid sequence of the precipitation effective portion will be the same as the penI protein, still more typically at least about 90 percent of the amino acid sequence of that effective portion will be the same as the sequence of the penI protein. Moreover, the precipitation effective portion will typically contain at least about 50 percent of the total number of amino acid residues of penI, more typically at least about 80 percent of the total residues of penI.

BRIEF DESCRIPTION OF THE DRAWINGS

FIG. 2 illustrates the nucleic acid sequences (SEQ ID NOS: 1–10) and amino acid sequences (SEQ ID NOS: 11–20) of fusion peptides of Examples 1 and 3. In the Figure, the sequence of the F1.2-C9 target peptide of the fusion polypeptide is underlined, and the point mutations of the other penI fusion polypeptides (designated as tFP010–tFP018 in the figure) prepared in Example 3 are also underlined.

FIGS. 6 and 7 show the results of the immunization of the PenI:C9 protein as detailed in Example 8.

DETAILED DESCRIPTION OF THE INVENTION

Figure 1:
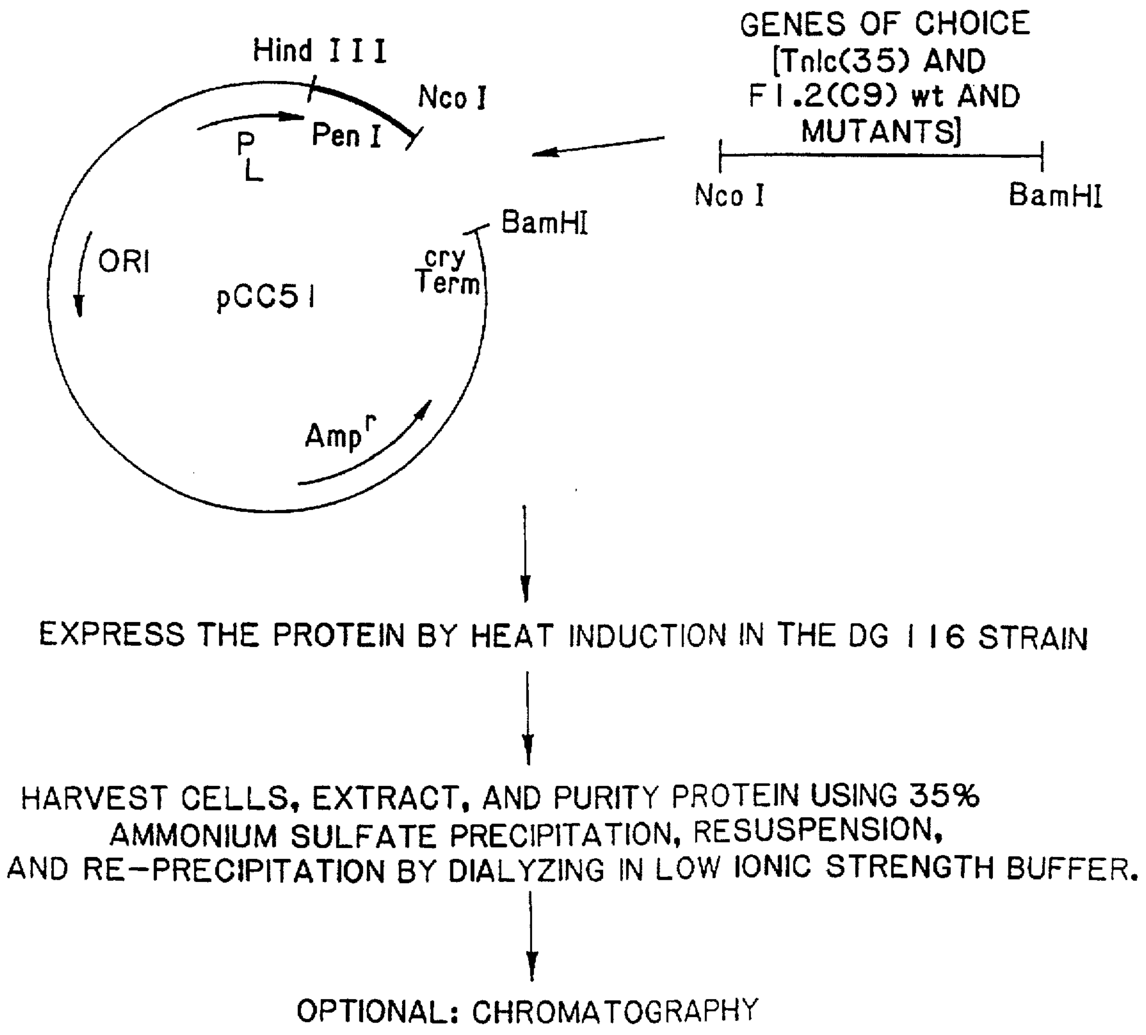
FIG. 1 illustrates the construction of the cloning vector pCC51 and use of that vector in accordance with the invention.

The present invention includes preparation of polypeptides by construction of DNA which encodes a fusion polypeptide, i.e. DNA which codes for the penI protein or precipitation effective portion thereof linked to the desired target peptide, which upon expression provides a polypeptide that comprises penI or portion thereof fused to the target peptide. The target peptide preferably is linked to the carboxyl terminus of penI protein or portion thereof, either directly or through a linking sequence. The target peptide suitably also may be linked to the amino terminus of the penI protein or portion thereof.

A fusion polypeptide also may be employed where the target peptide is flanked by portions of the penI protein whereby the flanked target peptide precipitates in a low ionic strength solution. Such a fusion polypeptide will contain two separate portions of the penI protein with the target peptide positioned therebetween. Preferably such a fusion polypeptide will contain two cleavage sites for release of the target peptide from the two "flanking" penI portions. This can be accomplished by interposing a linking segment on either side of the target peptide and between the penI protein portions, wherein those linking segments each can be recognized and cleaved by an appropriate cleavage agent.

In general, preparation of penI fusion peptides of the invention can be accomplished by recombinant DNA techniques, e.g. preparation of plasmid DNA, cleavage of DNA with restriction enzymes, ligation of DNA, transformation and culturing of host cells, etc., that are generally known to those skilled in the art and, e.g., disclosed generally in Sambrook, et al., Molecular Cloning, (2d ed. 1989).

More specifically, DNA is obtained coding for the penI protein or a precipitation effective portion thereof. One source of that DNA is *Bacillus licheniformis*, which is publicly available, e.g., from the American Type Culture Collection under Accession nos. 6598, 6634 and 8480. Isolation and cloning of such DNA has been described and includes molecular cloning and polymerase chain reaction. See Wittman, et al., *J. Bacteriol*, 170:3206–3212 (1988); and Himeno, et al., *J. Bacteriol.*, 168:1128–1132 (1986). See also Sambrook, et al., supra, including ch. 14 thereof. The nucleotide sequence coding for penI or portion thereof, or the sequence of other components of the fusion construct of the invention such as the sequence coding for the target peptide or linking segment, also can be synthesized by known methods, e.g. the phosphate triester method. See Oligonucleotide Synthesis, IRL Press (M. J. Gait, ed., 1984). Synthetic oligonucleotides also may be prepared using commercially available automated oligonucleotide synthesizers. The nucleotide and amino acid sequences of the penI protein are shown in FIG. 2 of the Drawings.

The gene coding for penI or effective portion thereof can be amplified by the polymerase chain reaction (PCR) or other means known in the art. Suitable PCR primers to amplify the penI gene may add restriction sites to the PCR product and include, e.g., an upstream primer of 5'-GGAAGCTTATGAAAAAAATACCTC-3' (SEQ ID NO: 21), and a downstream primer of

5'-GGGGATCCCTCACCATGGTTCCTTCTTTCTGTT-C-3' (SEQ ID NO: 22).

The penI gene can be amplified directly by standard PCR methods from *Bacillus licheniformis* chromosomal DNA using such primers or, alternatively, a suitable plasmid containing the penI gene can be used as the template for PCR. See Example 1 which follows.

To make the fusion vector, the sequence coding for penI or effective portion is linked to a sequence coding for the target protein by use of suitable ligases. DNA coding for the target peptide, optionally linked to DNA coding for a linking sequence, can be obtained by isolating the DNA from natural sources or by known synthetic methods as discussed above. A nucleotide sequence coding for penI or effective portion thereof may be directly joined to a DNA sequence coding for the target protein or, alternatively, a DNA sequence coding for a suitable linking sequence may be interposed between the sequence coding for penI and the sequence coding for the target peptide and joined using suitable ligases.

The linking sequence preferably is a nucleotide sequence that codes for a peptide that can be recognized and cleaved by a proteolytic agent that will cleave the fused polypeptide expressed by the gene construct to thereby provide the target peptide. A preferred linking sequence has a nucleotide sequence of ATCGAGGTAGG (SEQ ID NO: 23) and codes for the peptide Ile-Glu-Gly-Arg, which can be cleaved by blood coagulation factor Xa. See, for example, Nagai et al., *Nature*, 309:810–812 (1984). A variety of other linking sequences and cleavage agents can be employed as will be recognized by those skilled in the art.

Selection of a particular suitable agent will be based on the identity of the sequence of amino acid(s) at the intended cleavage site, particularly the identity of the linking sequence interposed between the penI protein or portion thereof and the target peptide. For example, suitable cleavage agents will include trypsin (cleaves at Arg, Lys), collagenase (cleaves at X-Gly-Pro), hydroxylamine (cleaves at Asn-Gly), dilute acid (cleaves at Asp-Pro), cyanogen bromide, N-bromosuccinimide, etc. Preferably the cleavage agent is selected so that it does not cleave the target protein, but reacts only with intended cleavage sites such as those positioned within the linking sequence and/or the penI protein or portion thereof. Thus, undesired cleavage can be minimized by use of cleavage agent that cleaves at a site present on the linking sequence but which is absent from the target peptide. Suitable linking sequences may be obtained by known means including oligonucleotide synthesis.

Other nucleotide sequences can be included in the gene fusion construct. For example, a promoter sequence, which controls expression of the sequence coding for the fused polypeptide, can be included in the construct or present in the expression vector into which the construct is inserted. A heat inducible promoter is particularly suitable. Similarly a signal sequence can be included in the gene construct, if desired, so that the expressed polypeptide can be secreted from the transformed host cells into the culture medium.

A number of strategies can be employed to express the fused polypeptide. For example, the gene fusion construct as described above can be incorporated into a suitable vector by known methods such as by use of restriction enzymes to make cuts in the vector for insertion of the construct followed by ligation. The vector containing the gene construct is then introduced into host cells for expression of the gene fusion. See, generally, Sambrook, et al., supra. Selection of suitable vectors can be made empirically based on factors related to the cloning protocol. For example, the vector should be compatible with, and have the proper replicon for the host cell that is being employed. Further the vector must be able to accommodate the DNA sequence coding for penI protein or portion thereof and the target peptide. Suitable host cells will include essentially any eukaryotic or prokaryotic cell, preferably those cells that can be easily transformed and exhibit rapid growth in culture medium. Specifically preferred host cells include prokaryotes such as *E. coli*, *Bacillus subtilis*, etc. and eukaryotes such as animal cells and yeast strains, e.g., a strain of the genus Saccharomyces such as *S. cerevisiae*. Other suitable hosts include, e.g., insect cells such as Sf9. The transformed host cells are typically multiplied in a selective growth medium, e.g. an antibiotic (assuming the cloning vector includes an appropriate resistance gene). The host cell containing the fusion vector is cultured and the fused gene is induced, if necessary, by conventional techniques.

In one suitable protocol the PCR product of the penI gene is cloned into a suitable vector such as the *E. coli* vector pUC19. Other vectors that may be suitably employed are known in the art, may be selected as disclosed above and include, e.g., pBR322. The isolated DNA coding for the target peptide is then cloned into the vector containing the penI gene. See, for example, FIG. 1 of the Drawings. The construct is then used to transform an appropriate host such as *E. Coli* by known methods. See Sambrook, et al., supra. As mentioned above, transformants are selected by conventional means e.g. by including an appropriate marker gene into the construct which imparts a detectable phenotypic property to transformed cells. For example, transformants can be identified by antibiotic (e.g. tetracycline) selection where the transformants contain the appropriate resistance gene. The host cell containing the fusion vector is cultured and the fused gene is induced, if necessary, by conventional techniques. For example, for at least certain systems, the cell culture can be suitably incubated by heating with agitation. The cells are then harvested and, if necessary or desired, lysed. The culture medium can be optionally centrifuged to remove various cell debris and other materials, and then is contacted with an aqueous solution having an ionic strength sufficient to precipitate the fused polypeptide. In one particularly preferred aspect of the invention, the fused polypeptide is precipitated from the culture medium or other solution by dialysis against a low ionic strength buffer, e.g., a solution having a salt concentration of about 250 or 200 mM or less, more preferably about 100 mM or less. A 50 mM KCl buffer solution is particularly preferred.

In general, the fused polypeptide will precipitate from a solution having a salt concentration of about 200 mM or less, typically from a salt concentration of about 200 mM to 50 mM. A dialysis procedure as described in Example 1 and elsewhere herein is a particularly preferred method for precipitating the fused polypeptide, although other methods for precipitating the polypeptide by contact with a low ionic strength buffer can be employed. For example, the penI fusion polypeptide in solution simply can be admixed with such a low ionic strength solution.

The conditions under which the polypeptide solution is contacted with the low ionic strength solution, e.g., rate of addition of buffer solution, temperature of buffer solution and polypeptide solution, etc., can be optimized with no more than routine experimentation to selectively precipitate the desired fusion polypeptide from other materials that may be present in the solution. For example, the fusion polypeptide solution can be contacted with the low ionic strength solution under selected conditions; yields and purity of the precipitated polypeptide obtained under the varying conditions will indicate the optimal parameters for precipitation of that polypeptide.

Similarly, suitable aqueous solutions having an ionic strength sufficient to precipitate the penI fusion polypeptide can be readily identified. For example, samples of a fusion polypeptide of the invention in solution can be treated with aqueous solutions having differing ionic strengths to thereby determine the optimum solution for precipitation of that fusion polypeptide.

The solution used to precipitate the fusion polypeptide preferably contains at least one salt. A number of salts known in the art may be employed including alkali metal or alkaline earth metal salts such as a sodium halide salt e.g. NaCl. It is generally preferred to employ a potassium salt, particularly a potassium halide such as KCl. The aqueous solution also typically contains a buffer such as Tris or other known agent to maintain pH at a desired level. The solution also may include other optional components, e.g., a protease inhibitor such as phenylmethylsulfonyl fluoride (PMSF).

It has been found that the initial concentration of the penI fusion polypeptide in solution prior to precipitation can affect recovery and purity of the precipitated polypeptide. Specifically, it is typically preferred that the fusion polypeptide be present in solution at a concentration of about 0.3 to 1.0 mg per millimeter of solution, although concentrations outside this preferred range also will be suitable, particularly higher concentrations. Such preferred concentrations of the fused polypeptide in a culture medium can be readily achieved in most cases, particularly when using the vector and heat induction system as described in Example 1 which follows. That vector and induction system typically results in expression wherein the penI-target peptide fusion constitutes about ≧20 wt. % of total cell protein.

It has been found that fusion polypeptides of the invention can be isolated in high purity from solution. For example, recombinant penI fusion polypeptides of the invention have been isolated from *E. coli* cells at a purity (HPLC analysis) of 50 percent or greater, and even at a purity of about 85 percent or greater.

It also has been found that penI fusion polypeptides of the invention can be isolated in high yields from a culture medium, e.g., at about 15 percent or greater of the total expressed polypeptide, and even yields of about 25 percent or greater. More specifically, the yield is often about 3 and 9 mg of polypeptide per $10^{11}$ *E. coli* cells. As will be appreciated by those skilled in this art, such yields are significantly higher than yields provided by prior isolation and purification methods.

The precipitated polypeptide may be employed without further purification or, optionally, it may be subjected to further purification steps. For example, the polypeptide can be dissolved in a suitable solution of relatively high ionic strength and then precipitated by contact with a low ionic strength buffer, particularly by dialysis against a low ionic strength buffer solution. The precipitated polypeptide also can be further purified by conventional techniques such as chromatography.

The purified polypeptide may be suitably used in its fused form, particularly where the biological properties of the target peptide are not deleteriously inhibited by the penI protein or portion thereof, or by the linking sequence (if present).

Alternatively, the target peptide can be released from the penI protein or portion thereof by treating the fused polypeptide with a suitable cleavage agent. In particular, if the polypeptide includes a linking segment as discussed above, the polypeptide can be treated with an appropriate cleavage agent to thereby cleave the polypeptide.

Virtually any peptide or protein can be purified in accordance with the present invention as long as the target peptide does not prevent precipitation of the fusion polypeptide of the invention (i.e., the peptide comprising the penI protein and the target peptide) in a low ionic strength buffer as specified above. Suitable target peptides can be readily identified by those skilled in the art, e.g., by sequential steps of 1) expressing a fusion vector as described above to provide a polypeptide that comprises penI or precipitation effective portion thereof and the target peptide of interest, 2) contacting that polypeptide in solution with a suitable low ionic strength buffer, and 3) observing the solution for precipitation of the polypeptide.

Certain characteristics of the target peptide either individually or in combination potentially can prevent or at least inhibit precipitation of a fusion polypeptide of the present invention. Specifically, the size of the target peptide and the number of charged moieties present on that peptide can affect precipitation of the fusion polypeptide. Thus, generally the target peptide comprises about 200 or less amino acids, more preferably about 140 or less amino acids, still more preferably comprising about 120 or less amino acids, even more preferably about 100 or less amino acids, most preferably about 70 to 80 amino acids or less. Larger target peptide portions could interfere with the ability of a fusion polypeptide to precipitate from solution. It is also preferred that the target peptide does not contain an excessive number of charged groups, i.e., either charged acidic or basic groups, which also could interfere with the ability of the polypeptide to precipitate from solutions of low ionic strength. Accordingly, preferably no more than about 10 to 20 percent of the total number of amino acids of the target protein are acidic or basic amino acids such as Lys, Arg, His, Asp or Glu.

Specific examples of peptides that can be synthesized and purified in accordance with the invention include, e.g., enzymes, transferases, lyases, isomerases, antigens or antigenic determinants, immunogens, proteins that form structural elements of animals, DNA binding peptides, peptides involved in protein/protein interaction, etc. Further, the invention is not limited to naturally occurring proteins, but also includes preparation and purification of synthetic peptides, i.e. peptides that do not occur in nature, including analogs of the above-mentioned proteins wherein one or more amino acids is different than the naturally occurring peptides, fragments of the above-mentioned naturally occurring peptides, and other synthetic peptides.

Polypeptides produced in accordance with the invention will have a wide variety of uses. For example, the fusion polypeptide can be used for immunization with penI or portion thereof acting as an antigenic carrier molecule for the target peptide. See, for instance, Example 8 which follows. Such a procedure is significantly more convenient than prior methods for use of non-immunogenic antigen. Those prior methods provide for chemical linkage of the previously prepared or isolated antigen to a carrier such as BSA or KLH followed by one or more purification steps. In contrast, by using penI as the carrier, an effective antigen can be prepared and isolated in high purity in a single step. These antigens can be used to produce polyclonal and monoclonal antibodies, specifically by administering a fusion polypeptide of the invention to a mammal such a mouse or rabbit, wherein that administration elicits a desired immune response, i.e., production of antibodies specific for epitope (s) of the polypeptide. The harvested antibodies can be used for a variety of applications as will be recognized by those skilled in the art including in various assays and diagnostics.

The invention also includes epitope mapping or epitope identification of a target peptide. In general, a peptide is prepared by the methods of the invention and the binding activity of that peptide with respect to a binding domain of a peptide or polypeptide (e.g., an antibody) is determined. The binding activity of a fusion peptide of the invention may be determined or, alternatively, the fusion peptide may be cleaved with an appropriate cleavage agent, the target peptide isolated, and the binding activity of the target peptide evaluated. More particularly, a group of penI fusion polypeptides having related sequences, e.g. each differing by only about 1–5 or 1–3 amino acids, can be isolated by contact with a low ionic strength buffer. To identify epitope (s) of the peptides, the binding activity of the isolated peptides to the binding domain of a particular peptide or polypeptide such as a monoclonal or polyclonal antibody can be determined through use of, e.g., a biosensor system using surface plasmon resonance detection, western blot analysis, or ELISA. See, for instance, Examples 3 and 4 which follow.

The invention also includes preparation and use of a random peptide library. For example, DNA sequences encoding a variety of peptides can be cloned into an expression vector system such as those identified above that contains a DNA sequence encoding the penI protein or precipitation effective portion thereof and, optionally, a linking sequence coding for a peptide sequence that contains one or more cleavage sites. Preferably restriction fragments of an appropriate cDNA library or genomic DNA library (see Sambrook, et al., supra) are used as the source of sequences inserted into the expression vector. Suitably those sequences are inserted in the expression vector downstream of the gene coding for penI or portion thereof and linking sequence, if present. Suitable host cells, e.g. those identified above such as *E. coli* cells, are transformed with the vector containing the gene fusion (i.e., the sequence coding for penI or portion thereof and the additional peptide). Transformants are cultured under suitable conditions, e.g. grown on a solid substrate such as a nylon membrane. The resulting cells are then screened for expression of fusion polypeptide(s) of interest by standard techniques such as by use of labelled antibody. See Methods in Enzymology, volume 152, Guide to Molecular Cloning Techniques, (S. Berger et al., ed., 1987). Polypeptides expressed from the selected clones then can be readily isolated and purified by contact with a low ionic strength solution to precipitate the polypeptide as disclosed above. The peptide of interest can be cleaved from the penI segment of the polypeptide if the polypeptide includes a suitable cleavage site such as a factor Xa site within a linking segment.

The invention also provides methods that comprise use of one or more fusion polypeptides of the invention to modulate the activity of T cells in vitro, e.g. to induce or enhance T cell proliferation or to inhibit or inactivate T cell development. The invention further provides in vitro assays to identify target peptides exhibiting activity to treat autoimmune diseases or to treat an undesired immune response such as those conditions discussed above, or to identify peptides useful in eliciting a desired immune response, as discussed above.

Typically T cells for such in vitro methods will be provided by transformed T cell lines such as T cell hybridomas or T cells which are isolated from a mammal, e.g., from a human or from a rodent such as a mouse. Suitable T cell hybridomas are publicly available or can be prepared by known methods. T cells can be isolated from a mammal by known methods. See, for example, Shimonkevitz, R., et al., (1983) J. Exp. Med. 158:303.

A suitable assay to determine whether a fusion polypeptide of the invention is capable of modulating the activity of T cells is conducted as follows, by the sequential steps 1–4 below. T cells suitably express a marker that can be assayed and that indicates T cell activation, or modulation of T cell activity after activation. Thus, e.g., as exemplified in Example 10 which follows, a T cell hybridoma such as the murine T cell hybridoma DO 11.10 that expresses interleukine-2 (IL-2) upon activation can be employed. IL-2 concentrations can be measured to determine if a particular presenting peptide is capable of modulating activity of the T cell hybridoma. Such a suitable assay is conducted by the following steps:

1. Antigen presenting cells are contacted with a fusion polypeptide of the invention that comprises a target peptide and a penI fusion protein or a precipitation effective portion thereof. A variety of antigen presenting cells can be employed including, e.g., monocytes, macrophages, dendritic cells and Langerhans cells. Specifically preferred antigen presenting cells for use in such an assay include A20 cells. Other suitable antigen presenting cells are disclosed in Edwin Walker, et al., Journal of Immunology, 128(5):2164–2169 (1982), particularly e.g. the L10A.6.2, L10A/2J, K46R, 2PK3, and P388D cells.
2. T cells carrying the T cell receptor specific to the fusion polypeptide are obtained such as from a T cell hybridoma of interest or by isolating from a mammal. The T cells are cultured under conditions that allow proliferation.
3. Proliferating T cells are contacted with the antigen presenting cells that have been previously contacted with a fusion polypeptide of the invention (see assay step 1. above).

4. After a period of such contacting with the antigen presenting cells, e.g. after 24 hours, modulation of the activity of the T cells by the fusion polyeptide is suitably measured by assaying the mixture for a marker, e.g. IL-2 production is measured. A decrease in IL-2 production, e.g., a 40 percent or greater decrease in IL-2 production after a period of 24 hrs., more typically a 50 percent or greater decrease in IL-2 production after a period of 24 hrs., indicates the fusion polypeptide modulates the activity of the T cells and can suppress an immune response.

It will be appreciated that the fusion polypeptide is first applied to antigen presenting cells, which are "professional" cells and capable of transporting the fusion polypeptide into the cells. An antigen presenting cell "loaded" with the fusion polypeptide can then react with T cells in such a cell to cell interaction.

The T cells employed in the assays are incubated under conditions suitable for proliferation. For example, a DO11.10 T cell hybridoma may be suitably incubated at about 37° C. and 5% $CO_2$ in complete culture medium (RPMI 1640 supplemented with 10% FBS, penicillin/streptomycin, L-glutamine and $5 \times 10^{-5}$M 2-mercaptoethanol). Serial dilutions of a fusion polypeptide of the invention can be added to the T cell culture medium. Suitable concentrations of the fusion polypeptide added to the T cells typically will be in the range of from $10^{-12}$ to $10^{-6}$M. T cell activation signals are provided by antigen presenting cells (APC) that have been loaded with the appropriate antigenic peptide. It is believed that use of antigen dose and APC numbers giving slightly submaximal T cell activation is preferred to detect inhibition of T cell responses with fusion polypeptide(s) of the invention. A decrease in production of IL-2 following contact with the fusion polypeptide indicates the fusion complex modulates activity of the T cells and can suppress immune response.

Alternatively, rather than measurement of an expressed protein such as IL-2, modulation of T cell activation can be suitably determined by changes in antigen-dependent T cell proliferation as measured by radiolabelling techniques as are recognized in the art. For example, a labeled (e.g., tritiated) nucleotide may be introduced to an assay culture medium. Incorporation of such a tagged nucleotide into DNA serves as a measure of T cell proliferation. This assay is not suitable for T cells that do not require antigen presentation for growth, e.g., T cell hybridomas. It is suitable for measurement of modulation by the penI fusion polypeptide of T cell activation for untransformed T cells isolated from mammals. A decrease in the level of T cell proliferation following contact with the fusion polypeptide(s) indicates the fusion complex modulates activity of the T cells and can suppress an immune response.

These in vitro assays can be employed to select and identify peptide(s), that are capable of modulating the activity of T cell receptor (including activation or inhibition of T cell development). Specifically, DNA sequences encoding either a library of random peptides or selected peptides can be cloned into an expression vector system such as those identified above that contains a DNA sequence encoding the penI protein or precipitation effective portion thereof and optionally, a DNA sequence coding for a peptide sequence that contains one or more cleavage sites. Transformation of suitable host cells and expression of the transformants can be carried out as described above. Suitably, restriction fragments of an appropriate cDNA of genomic DNA library (see Sambrook, et al., supra) are used as a source of the sequences inserted into the expression vector or, alternatively, selected oligonucleotides such as synthetic oligonucleotides of known sequence are used as the inserted sequence. Suitable hosts, such as a mammalian cells and others identified above, are transformed with the vector containing the gene fusion, e.g., the sequence coding for the peni protein or precipitation effective portion thereof linked to sequence coding for the target peptide. Transformants are cultured under suitable conditions and the cells are screened for expression of the fusion polypeptide of interest by contacting same with selected T cells. Assays described above, e.g., measurement of IL-2 production or T cell proliferation, are employed to determine if contact with the expressed fusion polypeptide modulates T cell activation. For example, a decrease in IL-2 production of APC-stimulated T cells identifies those fusion polypeptides that modulate activity of the T cells and can suppress immune responses. An increase in IL-2 production of such APC-stimulated T cells identifies those fusion polypeptides that can increase T cell responses and have use for vaccination applications.

All documents mentioned herein are incorporated by reference herein in their entirety.

The following non-limiting examples are illustrative of the invention.

EXAMPLE 1

To construct a suitable expression vector containing the penI gene, the penI gene was amplified by the Polymerase Chain Reaction (PCR) using standard techniques from the plasmid pCC34 as template. The plasmid pCC34 was a PUC19 vector containing the penI. Conditions of the PCR were as follows: 100 ng of the plasmid pCC34 was used as template, 10 pmoles of the primers FX-1 and FX-2 (identified immediately below), 50 mM KCl, 20 mM Tris-HCl pH 8.4, 2 mM $MgCl_2$, 100µg/ml Bovine Serum Albumin, 50 µM dNTP, 2.5 units of Taq DNA polymerase (Cetus Perkin-Elmer) in a 100 µl final volume. The reaction was run for 25 cycles at 95° C., 55° C. and 72° C. The penI gene also could be amplified by standard PCR techniques directly from *Bacillus licheniformis* chromosomal DNA using these same primers. The above-mentioned PCR primers used to amplify the penI gene were:

Upstream primer (FX-1)
5'-GGAAGCTTATGAAAAAAATACCTC-3' (SEQ ID NO: 24)

Downstream primer (FX-2)
5'-GGGGATCCCTCACCATGGTTCCTTCTTTCTGTTC-3' (SEQ ID NO: 25)

The upstream PCR primer was designed to add a HindIII restriction site at the 5' end of the PCR product and the downstream PCR primer was designed to add NcoI and BamHI restriction sites at the 3' end of the PCR product. The PCR product was digested with HindIII and BamHI and cloned into the HindIII-BamHI sites of the *E. coli* vector pUC19. As a result, this vector (tET002-3) contains the penI gene construct flanked by HindIII at the 5' end and NcoI and KpnI at the 3' end. The sequence of the cloned penI gene was confirmed using the ABI DNA sequencing apparatus and the M13 (+/−) universal sequencing primers.

To demonstrate that a fusion peptide could be expressed at high levels in *E. coli* the following oligonucleotides were designed and synthesized by the ABI oligonucleotide synthesizer:

Upstream Primer (ET003)
5'-
CATGGGACTCTGACCGTGCAATCGAAGGTCGTTGAGGGATCCGGTAC-3' (SEQ ID NO : 26)

Downstream
5'-CGGATCCCTCAACGACCTTCGATTGCACGGTCAGAGTCC-3' (SEQ ID NO : 27)

These oligonucleotide were annealed to each other as described below and cloned into the NcoI-KpnI site of the plasmid tET002-3. 100 pmoles of each oligonucleotide were boiled for 10 minutes in the presence of 44 rnM EDTA and 66 mM NaCl and cooled slowly to room temperature. These annealed oligos where cloned into the NcoI-KpnI sites at the 3' end of the penI gene. This plasmid was designated pCC50. The gene construct, from the HindIII site 5' of the penI gene to the BamHI site 5' of the KpnI site, was then subcloned into the expression vector pDG160, via the HindIII/BamHI sites, oriented 3' to the PL promoter. When properly expressed, this gene will encode the penI protein fused in frame to the following 9 amino acid peptide: Asp Ser Asp Arg Ala lleu Glu Gly Arg. The first two amino acid residues are P Y which are encoded by the NcoI codons and the following 9 amino acid residues designated C9 herein, are identical to the carboxy terminus of the factor Xa cleaved blood factor prothrombin. This plasmid was designed pCC51, and the oligonucleotide sequence between the NcoI and the SalI sites has also been confirmed as described above.

EXAMPLE 2

To express a large amount of the fusion peptide penI:C9, a 500 ml culture of strain DG116:pCC51 was grown in M9 medium (Per 1 liter volume, add 6 g of $Na_2HPO_4$ sodium phosphate dibasic, 3 g $KH_2PO_4$, 0.5 g NaCl and 1 g $NH_4Cl$ and autoclave. Make the following sterile additions: 10 ml of 20% glucose, 10 ml of 0.01M $CaCl_2$, 1 ml of 1M $MgSO_4$:$7H_2O$, 20 mg B1 (final concentration of 20 μg/ml), 5 g Casamino acids (Norit treated, final concentration 0.5%) and 50 μg/ml ampicillin) at 30° C. to an OD of 0.5–0.8. The culture was subjected to a heat shock to induce expression from the PL promoter of the plasmid by incubating it for 5–15 minutes at 42° C. The culture was then incubated with shaking at 39° C. for additional 1–2 hr. The cells were harvested and resuspended in 10 ml of Lysis Buffer (LB) (per 200 ml volume add: 20 ml of 1M Tris buffer [pH 8.0], 20 ml of 2M KCl, 0.8 ml of 0.25 EDTA, 04 ml of 1M $CaCl_2$, 1 ml of 2M $MgCl_2$, 20 μl of 0.1M DTT, 12.5 ml of 80% glycerol and 145.28 ml of H20). The cells were then disrupted in a french press at a pressure of 1500 PSI. The french press was washed with 10 ml of SB buffer (per 500 ml add: 50 ml of 1M Tris [pH 8.0], 10 ml of 1M $CaCl_2$, 0.5 ml of 1M DTT, 259 ml of 80% Glycerol and 189.5 mls of $H_2O$)+200 mM KCl. The final volume was recorded at 17 ml. A 10% solution of polyethyleneimine was slowly added to a final concentration of 0.6%. The sample was centrifuged at 4° C. at 6000 RPM in a Beckman J2-HS rotor JA-20. The supernatant was removed and saved. To extract pellet (DNA) associated protein, the pellet was resuspended in 5 ml of SB buffer+600 mM KCl and was shaken at 4° C. for 1 hr. The sample was then centrifuged and the supernatant was added to the saved one. The combined supernatant was stirred in an ice bath and ammonium sulfate was slowly added to a final concentration of 35% w/v. The sample was centrifuged at 4° C. at 6000 RPM for 1 hr and the pellet kept. The pellet was redissolved in 10 ml of SB buffer+50 mM KCl, loaded into a dialysis bag and dialyzed with 2 changes of 400 mls of buffer overnight at 4° C. overnight. The precipitated material is collected by gentle centrifugation, washed with SB+50 mM KCl. The pellet is redissolved in 300 μl of 2M KCl, and add 100 μl of 10× SB buffer and slowly add 600 μl of $H_2O$) (final buffer concentration was SB+600 mM KCl). To evaluate the purity of the penI:C9 a 20 μl sample is resolved on a 12.5–15% SDS-PAGE.

EXAMPLE 3

To examine the effect of each of the nine amino acid residues in the peptide C9, each was separately substituted with alanine, except the alanine in position 5 which was substituted with serine. See FIG. 2 where the DNA and amino acid sequences of each of the muteins (labeled tFP010-tFP018) are identified. To construct the vectors expressing these PenI:C9 muteins, the following complementary oligonucleotide pairs containing the codon for alanine in each position of the C9 peptide were designed:

KM1-1 upstream
CATGGGCATCTGACCGTGCAATCGAAG-GTCGTTGAGG (SEQ ID NO: 28)
KM1-2 downstream
GATCCCTCAACGACCTTCGATTGCACG-GTCAGATGCC (SEQ ID NO: 29)
KM2-1 upstream
CATGGGACGCTGACCGTGCAATCGAAG-GTCGTTGAGG (SEQ ID NO: 30)
KM2-2 downstream
GATCCCTCAACGACCTTCGATTGCACG-GTCAGCGTCC (SEQ ID NO: 31)
KM3-1 upstream
CATGGGACTCTGCACGTGCAATCGAAG-GTCGTTGAGG (SEQ ID NO: 32)
KM3-2 downstream
GATCCCTCAACGACCTTCGATTGCACGT-GCAGAGTCC (SEQ ID NO: 33)
KM4-1 upstream
CATGGGACTCTGACGCTGCAATCGAAG-GTCGTTGAGG (SEQ ID NO: 34)
KM4-2 downstream
GATCCCTCAACGACCTTCGATTG-CAGCGTCAGAGTCC (SEQ ID NO: 35)
KM5-1 upstream
CATGGGACTCTGACCGTTCCATCGAAG-GTCGTTGAGG (SEQ ID NO: 36)
KM5-2 downstream
GATCCCTCAACGACCTTCGATGGAACG-GTCAGAGTCC (SEQ ID NO: 37)
KM6-1 upstream
CATGGGACTCTGACCGTGCAGCTGAAG-GTCGTTGAGG (SEQ ID NO: 38)
KM6-2 downstream
GATCCCTCAACGACCTTCAGCTGCACG-GTCAGAGTCC (SEQ ID NO: 39)
KM7-1 upstream
CATGGGACTCTGACCGTGCAATCGCTG-GTCGTTGAGG (SEQ ID NO: 40)
KM7-2 downstream
GATCCCTCAACGACCAGCGATTGCACG-GTCAGAGTCC (SEQ ID NO: 41)

KM8-1 upstream
CATGGGACTCTGACCGTGCAATCGAAG-CACGTTGAGG (SEQ ID NO: 42)
KM8-2 downstream
GATCCCTCAACGTGCTTCGATTGCACG-GTCAGAGTCC (SEQ ID NO: 43)
KM9-1 upstream
CATGGGACTCTGACCGTGCAATCGAAG-GCGCATGAGG (SEQ ID NO: 44)
KM9-2 downstream
GATCCCTCATGCGCCTTCGATTGCACG-GTCAGAGTCC (SEQ ID NO: 45)

The oligonucleotide pairs were annealed to each other as described before, cloned into the NcoI-BamHI site of the vector pCC50 and the DNA sequence was confirmed as described before, and the entire PenI:C9 constructs were subcloned into the pDG160 expression vector as described before. Each of these plasmids was introduced into the *E. coli* strain DG116 as described before, and the cognate penI:C9 peptides expressed and purified as described above. The binding of the purified PenI:C9 muteins to the TA1 antibody (TA1) was examined by several methods: 1. Western-Blot analysis, 2. ELISA, and 3. BIACore Analysis.

EXAMPLE 4

In order to analyze the different binding of the different PenI:C9 muteins to the TA1 antibody (TA1 was raised from a mouse that had been immunized with F1.2-C9 KLH by standard procedures; F1.2-C9 is the purified factor Xa cleavage product of prothrombin), a biosensor system using surface plasmon resonance detection (BIAcore, Pharmacia Biosensor) has been used. This system records the binding of the antigen to the immobilized TA1 in real time.

TA1 has been chemically immobilized onto the carboxymethylated dextran matrix of the sensor chip (CM5) using the amine coupling kit and the method provided by the manufacturer (Pharmacia Biosensor). For this purpose TA1 was diluted to 57 μg/mL in 10 mM Na-acetate buffer pH4. After activation of the sensor chip with 30 μl of a 1:1 mixture of 11.5 mg/mL N-hydroxysuccinimide (NHS) and 75 mg/ml N-ethyl-N'-(dimethylaminopropyl) carbodiimide (EDC) 5 μL of the TA1 solution was injected at a flow rate of 3 μL/min. Residual dextran binding sites were inactivated by treatment of the chip surface with 37 μL of 1M ethanolamine pH 8.5. This resulted in the immobilization of 4541 resonance units (RU) of TA1.

The mono-S chromatography purified PenI:C9 muteins, PenI:C9 wild type (identified in Examples 1 and 3 above and FIG. 2) and the native PenI alone were diluted to 30 μg/mL in eluent buffer containing P20 (10 mM HEPES, 150 mM NaCl, 3.4 mM EDTA, 0.005% P20 surfactant, pH 7.4) of the biosensor system. The BIAcore program was set up as follows: Flow rate: 5 μl/min. Injection of 25 μL of PenI-peptide. Injection of 5 μL of 25 mM NaOH which regenerates TA1 by stripping of the PenI:C9 peptide. Report points were set 1. at 10 sec before the sample injection (baseline), 2. at 10 sec before the NaOH injection and 3. at 100 sec after the NaOH injection (regeneration).

Figure 3:
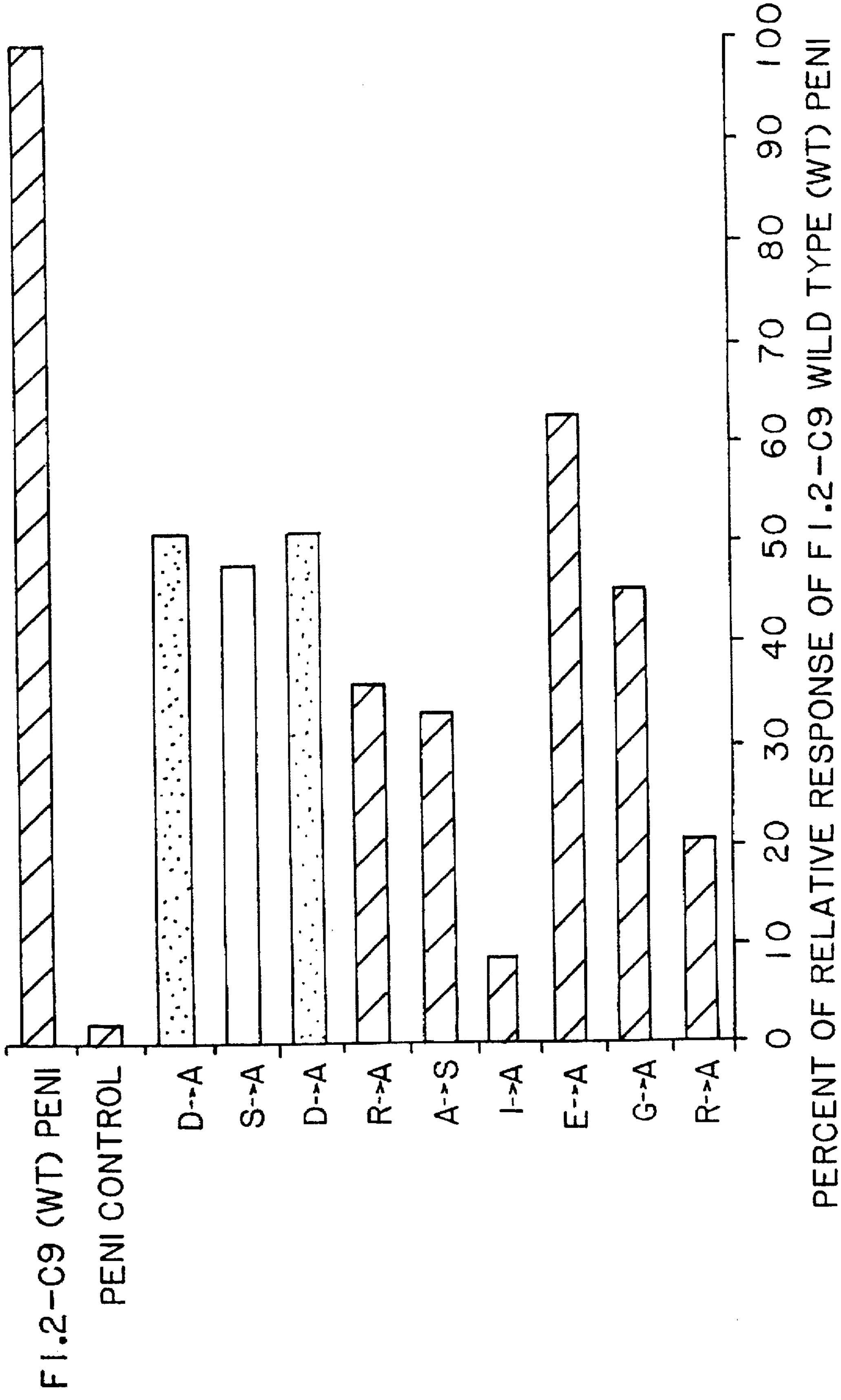
FIG. 3 shows the results of the real time Biospecific Interaction Analysis (BIAcore analysis) of Example 4.

Each PenI:C9 and the native PenI protein was injected according to this program and a relative response in RU which represent the amount of penI:C9 mutein bound, was calculated by subtracting the RU of report point 1. from report point 2. Percent of binding was then calculated by setting the relative response of the wild type to 100%. Native PenI containing no C:9 fusion peptide, didn't show a significant binding (<5%) to TA1. The seven PenI:C9 muteins showed 65–35% less binding to Ta1 as compared to the wild type PenI:C9. The binding results are detailed in FIG. 3 of the Drawings. The most dramatic reduction of binding was noticed when the isoleucine in the C9 peptide has been substituted with alanine; in this case the binding was only 10% compared to the wild type PenI:C9. The substitution of the carboxy terminal arginine to alanine also resulted in a significant reduction of binding to TA1 to only 20% compared to the wild type.

EXAMPLE 5

Expression of a PenI:TroponinI and PenI:SH2 Fusions

Additional penI fusion polypeptides were expressed and isolated, the first including a target peptide containing the 35 amino acid TroponinI epitope (amino acids 26–60, TnI 35, of the mature human TroponinI, 10 which is recognized by the monoclonal antibodies (mAB's) 2F6.6 and 2B1.9), and the second fusion containing a target peptide portion of the SH2 domain of GAP-N.

The DNA fragment encoding TnI35 was amplified by standard PCR techniques from a plasmid containing the TnI gene with the following primers:

Forward primer RTB#29:
GGGGCCATGGATCGAAGGTCGTAC-TAGTCGCGCTTATGCCACG
(SEQ ID NO: 46) and the backward primer RTB#30:
CCCCGGATCCTCACAGCTCTTGCTTTGCAATCGT
(SEQ ID NO: 47).

Figure 4:
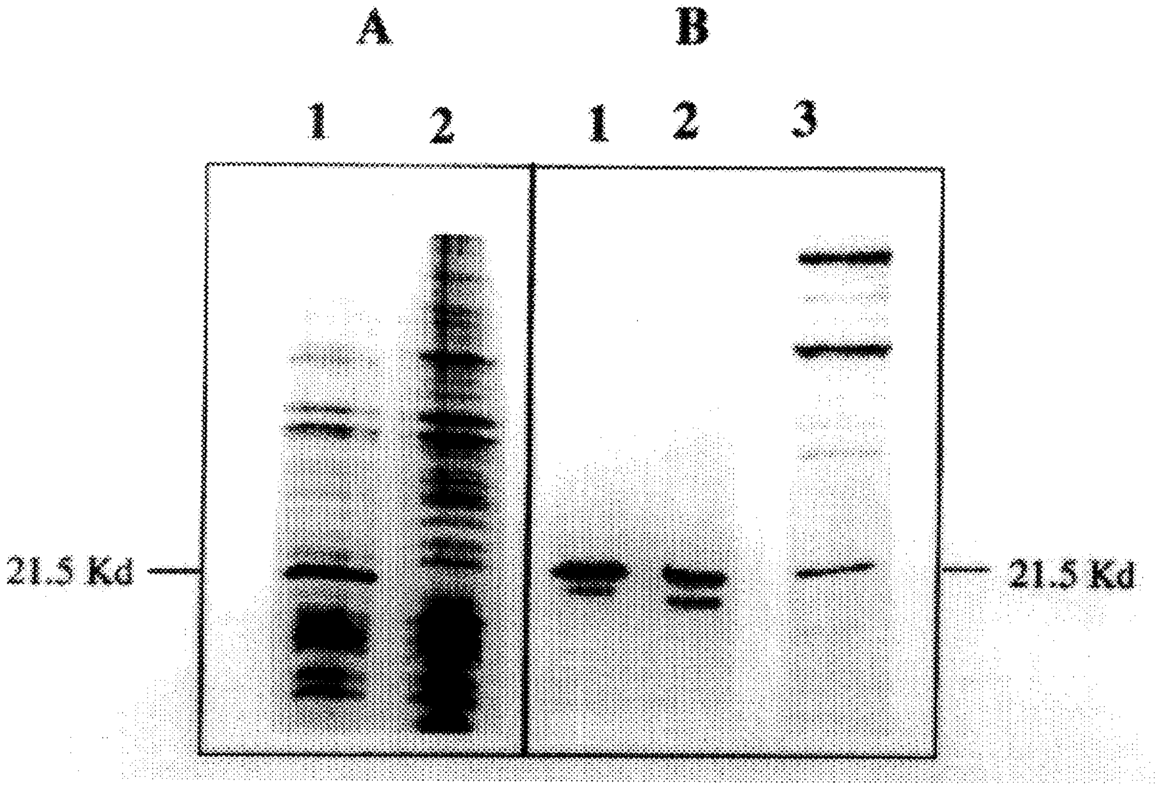
FIG. 4 shows the Western Blot and SDS polyacrylamide gel electrophoresis gel of PenI:Troponin fusion protein produced and purified in accordance with the invention. In that Figure, lane A-1 is the SDS PAGE of induced/total protein; lane A-2 is the SDS PAGE of uninduced/total protein; lane B-1 shows post cell breakage/western blot/total protein; lane B-2 shows purified (35% ammonium sulfate cut)/western blot; and lane B-3 shows purified (35% ammonium sulfate cut)/SDS PAGE.

The PCR product was digested with NcoI and BamHI and cloned into the vector pCC51 as described in Example 1 above. The resulting plasmid pCC51:PenI-TnI 35 was introduced into the *E. Coli* strain DG116 and the resulting strain was induced for expression of the fusion protein as described in Example 1 above. The soluble fraction of these cells was processed as described before and the purified fusion peptide was analyzed by SDS-PAGE and Western-Blot analysis. See FIG. 4. The results indicated that this fusion peptide is expressed up to 20% of total cell protein. The fusion peptide was purified as described in Example 1 above except that 10 mM PMSF was added to the buffers used throughout the purification process. Approximately 40% of the recovered peptide has been processed from its carboxy terminus during the purification process, suggesting that this fusion peptide may be labile under these conditions although it is stable intracellularly.

Similarly, the SH2 domain of GAP-N (92 amino acids in length) was fused to the PenI gene. The DNA fragment encoding the SH2 domain was cloned as follows. An overlap PCR was done using the primers:

CLC 107 upstream
GAGAGAAAGCTTATGAAAAAAATACCTCAAAT (SEQ ID NO : 48)
CLC 108 downstream
GGAGCCGCCACCACCGCTGCCACCACCGCCAGAACCGCCGCCACCTTCCTT CTTTCTGTTCTTAT (SEQ ID NO : 49)

CLC 109 upstream

-continued

GGTGGCGGCGGTTCTGGCGGTGGTGGCAGCGGTGGTGGCGGCTCCTGGTGGTATCACGGAAAACTTGA (SEQ ID NO : 50)

CLC 119 downstream

CCTTCCGGATCCTCATCAAACTGGGTAAAGTAATTTTT (SEQ ID NO : 51)

CLC 107 and CLC 108 were used in a PCR reaction with a DNA template containing PenI gene. CLC 107 places a HindIII site at the 5' end of the PenI and CLC 108 places a 15 amino acid linker at the 3' end. CLC 109 and CLC 119 were used in a PCR reaction with a DND template containing the GAP-N SH2 gene. CLC 109 places the 15 amino acid linker at the 5' end of the GAP-N SH2 and CLC 119 places a BamHI site at the 3' end. The resulting PCR products from each reaction were then added together in a new PCR reaction with CLC 107 and CLC 119. The resulting fragment containing PenI-linker-SH2 was digested with HindIII and BamHI and then ligated into the pDG160 expression vector and into the vector pTRP3 downstream from the *E. coli* Trp promoter.

This fusion peptide was expressed in *E. coli* and purified as described in Example 1 above. The results indicate that it is also processed during the purification, similar to the PenI:TnI35 fusion peptide. To maximize recovery of the full length fusion polypeptide from the pDG160 vector 1–10 mm PMSF are added to the cell before breakage. To maximize recovery from the pTRP3 construct the culture is grown at 30° C.

EXAMPLE 6

Comparison of PenI:C9 Muteins vs PenI:C9 wt by Competition ELISA

Figure 5:
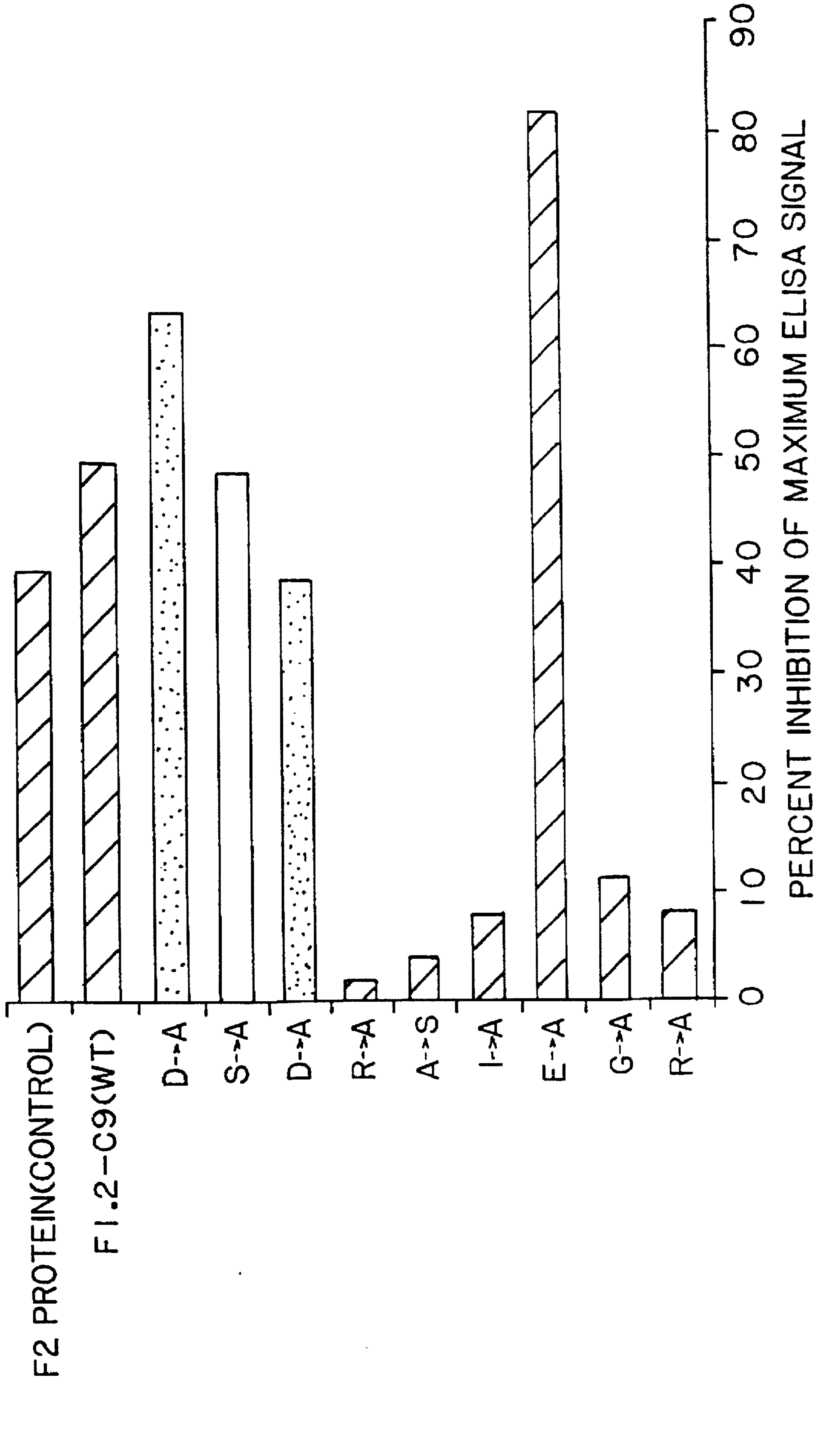
FIG. 5 shows the results of the competitive ELISA assay of the fusion peptide of Example 6.

The HPLC monoS purified PenI:C9 muteins and wild type (wt) (identified in Examples 1 and 3 above and FIG. 3) were tested for their relative binding to the anti-C9 specific protein A purified mAb TA1 in a competitive ELISA. The assay was performed using microtiter plates that had been previously coated with PenI:C9 (wt) by a passive technique (10 μmng protein/well). Dilution of the PenI:C9 (wt) and the PenI:C9 mutein, were preincubated for 1 hour at room temperature with the mAb TA1 that was at a concentration of 271 ng/ml. The plates were washed and 100 μl/well of each sample was applied and incubated at room temperature for ½ hour. The wells were washed and 100 μl/well of a 1:2000 dilution of a Goat anti-mouse IgG HRP conjugate was added. The plated were incubated at room temperature for another ½ hour. The plates were washed again and 100 μl/well of substrate (ABTS) was added and allowed to react for 8 minutes at room temperature. Each well was quenched with 100 μl of 1% SDS stop solution. The ELISA signal was read at 405 nm using a Biotek Plate reader. The data collected was analyzed using EXCEL 4.0 software. The maximum (100%) ELISA signal was determined as the average of values seen for dilution of penI lacking C9 that was allowed to react with TA1 as described above. Inhibition of TA1 binding was compared for all PenI:C9 muteins and PenI:C9 (wt) by using the ELISA signals measured at a concentration of 0.2 μM of the competing PenI:C9 fusion protein. This was the concentration at which PenI:C9 (wt) generated a 50% signal compared to the maximum signal generated in this ELISA. FIG. 5 of the Drawings shows this data expressed as percent binding to TA1 in a bar graph. The results clearly indicate that not all nine amino acid residues are required for binding. The amino terminus of the peptide DSDRAIEGR is shown to be less important to binding to TA1 relative to the carboxy terminus of the peptide. More specifically, the results indicate that the sequence RAIXGR of the peptide contributes to most of the binding of the peptide.

EXAMPLE 7

Cleavage and Purification of the Troponin I 35 Amino Acid Peptide from PenI:TnI Fusion Polypeptide To purify the TnI35 peptide from the fusion protein PenI:TnI135, 23.7 μg of purified PenI:TnI35 were digested with 0.004 units of F:actor Xa (Sigma Diagnostics 870-10) at 37° C. for 30 minutes. The sample was then brought to 0.1% trifluoroacetic acid (TFA) and loaded onto a prepacked Pharmacia PepRPC C2/C18 reverse phase column (0.5×6 cm, 5 μm particle size), equilibrated with 0.1% TFA in water (solvent A) and connected to a Waters 625 Liquid Chromatography System. The column was eluted with a linear gradient of 0–100% solvent B (0.1% TFA in acetonitrile) in 20 minutes at a flow rate of 1 ml/min. The absorbance of 214 nm was monitored to detect the eluted peptide. The retention time for TnI35 cleaved peptide was 12.2 minutes. This retention time was identical to the identical synthetic peptide run as a control.

EXAMPLE 8

Immunization of Mice with PenI:C9

Part 1. To show the efficacy of the fusion peptide PenI:C9 as a carrier for immunization, Balb/c mice were immunized with F1.2-C9 conjugated to KLH or the F1.2-C9 penI fusion polypeptide of the invention (see Examples 1 and 3 above and FIG. 2) by either intraperitoneal or subcutaneous injection in complete or incomplete Freund's adjuvant respectively as described in the Table shown in FIG. 6 of the Drawings. In that Table the designation "CFA" refers to Complete Freund's Adjuvant, "IFA" refers to Incomplete Freund's Adjuvant, "i.p." refers to intraperitoneally, and "subcut." refers to subcutaneously. Dates of injection are given with reference to the date of sensitization (day 1).

Part 2. The immunized mice were bled and assayed for specific antibody response to the C9 peptide as generally described in the Table shown in FIG. 7 of the Drawings. Specifically, the mice were immunized on day 70 (first boost) and day 101 (second boost) after sensitization with F1.2-C9 KLH #3 and on day 32 after sensitization with the fusion polypeptide F1.2-C9 penI #1 and assayed for specific antibody response to the F1.2-C9 peptide and F2 (truncated F1.2 protein) by a sandwich ELISA assay with antigen (F2 or F1.2-C9 synthetic peptide conjugated to KLH or Ova) coated microtiter plate wells. Controls included sera of mice immunized previously with F1.2-C9 conjugates and TA1 monoclonal (TA1 was raised from a mouse that had been immunized with F1.2-C9 KLH by standard procedures). The titer was deterimined as the highest dilution producing an ELISA signal equal to or greater than twice that of background.

The results as shown in the Table of FIG. 7 indicated that the mice responded to the PenI:C9 peptide in titers comparable to those of mice immunized with synthetic peptide KLH conjugant.

EXAMPLE 9

Construction and Expression of a Recombinant Fusion Polypeptide of the Invention (PenI:Ova fusion protein)

To construct a plasmid expression a recombinant PenI:Ova protein the following coinplementary oligonucleotides were designed and synthesized by the ABI oligonucleotide synthesizer:

MB1
CATGGATCGAAGGTCGTATCAGCCAGGCTGTTCACGCAGCTCACGCAGAAATCAACGAAGCTGGTCGTTGAG (SEQ ID NO : 52); and MB2
GATCCTCAACGACCAGCTTCGTTGATTTCTGCGTGAGCTGCGTGAACAGCCTGGCTGATACGACCTTCGATC (SEQ ID NO : 53

100 pmole of each oligonucleotide were annealed to each other as described in Example 1 above and cloned into the NcoI-BamHI site of the plasmid pCC51 at the 3' end of the penI gene. Thus this gene encodes a penI protein fused in frame to the following 21 amino acid peptide: IEGRISQAVHAAHAEINEAGR (SEQ ID NO: 54) at the carboxy terminus. The first four amino acid residues represent a factor Xa cleavage site and the following 17 amino acid residues are identical to the Ova peptide (A. Sette et al., *Nature* 328:395 (1987)). The resulting plasmid was designated pMB01, and the oligonucleotide sequence of the between the NcoI and the BamHI sites has also been confirmed. This plasmid was transferred into the *E.coli* strain DG116 and the fusion protein PenI:Ova was expressed and purified as described in Example 2 above. 1.4 mg of highly purified PenI:Ova were recovered after conducting a mono-S chromatography purification.

EXAMPLE 10

Activation of Antigen Presenting Cells and Stimulation of T Cells

The efficacy of a fusion polypeptide of the invention to load APCs and activate T cells was tested. A penI:Ova fusion polypeptide (i.e., a fusion polypeptide containing the penI protein linked to an Ova target peptide) was employed as well as other materials. Three independent experiments were performed utilizing A20 APC and the D011 T cell myeloma cell line. D011 cells are specifically responsive to Ova loaded major histocompability complex class II (MHCII) molecules presented by A20 APCs. A20 cells were loaded with 5 μg purified penI:Ova fusion polypeptide or 5 μg synthetic Ova peptide (positive control synthesized by Mimetics, Chiron Corp.) for 1 hour. $1\times10^5$ D011 cells were added and incubated with the loaded A20 cells for 24 hours. The degree of activation of D011 cells was determined by the release of Interleukin 2 (IL-2) into the culture medium. After 24 hours of incubation supernatants were collected and analyzed in an ELISA format for IL-2 (using two anti-IL2 antibodies from Pharmacia).

The following Table summarizes the results of the three experiments and includes several negative controls. One of these controls is a PenI:Ova fusion protein containing the hen egg lysozyme (HEL) peptide preceded by the Factor Xa cleavage recognition site IEGRNLCNIPCSALLSS (SEQ ID NO: 55) and therefore should not stimulate D011 cells.

The PenI:HEL fusion protein was constructed exactly as PenI:Ova except the following oligonucleotide pair was used:

MB3
CATGGATCGAAGGTCGTAACCTATGCAACATCCCGTGCAGCGCACTGCTGAGCAGCTGAG (SEQ ID NO : 56); and

MB4
GATCCTCAGCTGCTCAGCAGTGCGCTGCACGGGATGCATAGGTTACGACCTTC (SEQ ID NO : 57)

TABLE

| | IL-2 release pg/ml | | |
|---|---|---|---|
| | Experiment 1 | Experiment 2 | Experiment 3 |
| DO11 cells only | 0 | 0 | 0 |
| A20 cells only | 0 | 0 | 0 |
| DO11 and A20 cells | 0 | 0 | 0 |
| DO11 and PenI:Ova | 0 | 0 | 0 |
| DO11 and Ova | 0 | 0 | 0 |
| DO11 and A20 and PenI | 0 | 0 | 0 |
| DO11 and A20 and PenI:HEL | 0 | 0 | 0 |
| DO11 and A20 and elution buffer | 0 | 0 | 0 |
| DO11 and A20 and PenI:Ova | 6690 | 11198 | 8805 |
| DO11 and A20 and Ova | 8786 | 11146 | 6778 |

The results set forth in the above Table show that the Ova peptide and the peni:Ova fusion polypeptide, but none of the negative controls, stimulated D011 cells. The results set forth in the Table indicate the penI:Ova peptide is as effective as the Ova peptide itself in stimulating D011 cells. The results also indicate the penI:Ova fusion peptide is transported and processed by A20 APCs and properly presented to the D011 TCR (T cell receptor) in the context of MHCII molecules.

EXAMPLE 11

Efficacy of PenI:Ova Compared to Ova Peptide

To demonstrate that the penI:ova protein fusion polypeptide was as effective as Ova peptide on a molar basis in stimulating D011 cells, three titration experiments were performed, designated as Experiment 1, Experiment 2 and Experiment 3 in the Tables A and B below. Equimolar amounts of penI:Ova and Ova peptide were used in the A20/D011 activation assay that was conducted as described in Example 10 above. The results are summarized in the following Table A and Table B.

TABLE A

| moles Ova | IL-2 released pg/ml | | |
|---|---|---|---|
| peptide per well | Experiment 1 | Experiment 2 | Experiment 3 |
| $2.4 \times 10^{-9}$ | — | 4624 | 3675 |
| $1.2 \times 10^{-9}$ | — | 3702 | 2997 |
| $6.0 \times 10^{-10}$ | 4011 | 3487 | 2023 |
| $3.0 \times 10^{-10}$ | 3333 | 2714 | 742 |
| $1.5 \times 10^{-10}$ | 1878 | 1284 | 0 |
| $7.4 \times 10^{-11}$ | 589 | 216 | 0 |
| $3.7 \times 10^{-11}$ | 0 | 0 | 0 |

TABLE B

| Moles of penI:Ova fusion | IL-2 released pg/ml | | |
|---|---|---|---|
| polypeptide per well | Experiment 1 | Experiment 2 | Experiment 3 |
| $2.4 \times 10^{-9}$ | 5267 | — | 3049 |
| $1.2 \times 10^{-9}$ | 3420 | — | 1452 |
| $6.0 \times 10^{-10}$ | 1624 | 2944 | 170 |
| $3.0 \times 10^{-10}$ | 144 | 675 | 0 |
| $1.5 \times 10^{-10}$ | 0 | 0 | 0 |
| $7.4 \times 10^{-11}$ | 0 | 0 | 0 |
| $3.7 \times 10^{-11}$ | 0 | 0 | 0 |

To calculate the relative activity of PenI:Ova and Ova peptide in Experiment 1 the IL-2 level released for $6.0\times10^{-11}$ moles/well of PenI:Ova (1624 pg/ml) was backfitted on the IL-2 curve for Ova alone to give $1.9\times10^{-10}$ moles Ova/well. Dividing the backfit value ($1.9\times10^{-10}$) by the actual moles of Ova added per well ($6\times10^{-11}$) gives 3. Hence, PenI:Ova is three times more effective on a molar basis than Ova peptide alone in stimulating D011 cells. This experiment was repeated twice (Experiments 2 and 3) and the results indicate that in Experiment 2 and 3 PenI:Ova is 16 times and 8 times more effective on a molar basis, than Ova peptide, respectively.

This invention has been described in detail with reference to preferred embodiments thereof. However, it will be appreciated that those skilled in the art, upon consideration of this disclosure, may make modifications and improvements within the spirit and scope of the invention.

What is claimed is:

1. A method for identification of a peptide that can modulate the activity of T cells, comprising 1) contacting antigen presenting cells with a fusion polypeptide that comprises a target peptide and a peni protein or precipitation effective portion thereof; and then 2) contacting the antigen presenting cells with T cells.

2. The method of claim 1 wherein the antigen presenting cells are contacted with the fusion polypeptide and T cells in vitro.

3. The method of claim 1 wherein the fusion polypeptide further comprises a linking sequence.

4. The method of claim 3 wherein the linking sequence comprises a cleavage site.

5. The method of claim 1 the penI protein or precipitation effective portion thereof is derived from *Bacillus licheniformis.*

6. The method of claim 1 wherein the penI protein or precipitation effective portion thereof has at least about 50% amino acid identity to *Bacillus licheniformis* penI protein.

7. The method of claim 1 wherein the penI protein or precipitation effective portion thereof has at least about 70% amino acid identity to *Bacillus licheniformis* penI protein.

8. The method of claim 1 wherein the penI protein or precipitation effective portion thereof has at least about 90% amino acid identity to *Bacillus licheniformis* penI protein.

9. The method of claim 8 wherein the penI protein or precipitation effective portion thereof is derived from *Bacillus licheniformis* and the target peptide has about 200 amino acid residues or less.

10. The method of claim 1 wherein the target peptide has about 200 amino acid residues or less.

11. The method of claim 2 wherein proliferation of the T cells is induced or enhanced by contact with the antigen presenting cells.

12. The method of claim 2 wherein proliferation of the T cells is inhibited by contact with the antigen presenting cells.

13. A method for identification of a peptide that can modulate the activity of T cells, comprising contacting T cells with a fusion polypeptide that comprises a target peptide and a penI protein or precipitation effective portion thereof.

14. The method of claim 13 wherein the T cells are contacted with the fusion polypeptide in vitro.

15. The method of claim 13 wherein the fusion polypeptide further comprises a linking sequence on either side of the target peptide and between the flanking precipitation effective penI protein portions.

16. The method of claim 13 wherein the linking sequence comprises two cleavage sites.

17. The method of claim 13 the peni protein or precipitation effective portion thereof is derived from *Bacillus licheniformis.*

18. The method of claim 13 wherein the penI protein or precipitation effective portion thereof has at least about 50% amino acid identity to *Bacillus licheniformis* penI protein.

19. The method of claim 13 wherein the penI protein or precipitation effective portion thereof has at least about 70% amino acid identity to *Bacillus licheniformis* penI protein.

20. The method of claim 13 wherein the penI protein or precipitation effective portion thereof has at least about 90% amino acid identity to *Bacillus licheniformis* penI protein.

21. The method of claim 20 wherein the penI protein or precipitation effective portion thereof is derived from *Bacillus licheniformis* and the target peptide has about 200 amino acid residues or less.

22. The method of claim 13 wherein the target peptide has about 200 amino acid residues or less.

23. The method of claim 13 wherein proliferation of the T cells is induced or enhanced by contact with the antigen presenting cells.

24. The method of claim 13 wherein proliferation of the T cells is inhibited by contact with the antigen presenting cells.

* * * * *

SEQUENCE LISTING ( 1 ) GENERAL INFORMATION:

( i i i ) NUMBER OF SEQUENCES: 57

( 2 ) INFORMATION FOR SEQ ID NO:1:

( i ) SEQUENCE CHARACTERISTICS:
( A ) LENGTH: 433 base pairs
( B ) TYPE: nucleic acid
( C ) STRANDEDNESS: unknown
( D ) TOPOLOGY: unknown ( x i ) SEQUENCE DESCRIPTION: SEQ ID NO:1:

```
AAGCTTATGA AAAAAATACC TCAAATCTCT GATGCGGAAT TAGAAGTGAT GAAAGTCATC    60
TGGAAGCATT CTTCGATCAA TACCAATGAG GTAATTAAAG AGTTATCCAA AACCAGTACA   120
TGGAGCCCTA AAACCATCCA AACCATGCTG CTGCGCCTCA TTAAAAAAGG CGCTTTAAAC   180
CACCATAAAG AAGGACGGGT TTTCGTTTAC ACACCAAATA TAGACGAAAG TGATTATATA   240
GAGGTTAAGA GTCACAGTTT TTTAAACCGG TTTTACAATG GAACTCTTAA TTCGATGGTA   300
TTAAACTTTT TGGAGAATGA TCAGCTGTCA GGTGAAGAAA TTAATGAATT GTATCAAATA   360
TTAGAAGAAC ATAAGAACAG AAAGAAGGAA CCATGGGACT CTGACCGTGC AATCGAAGGT   420
CGTTGAGGGA TCC                                                      433
```

( 2 ) INFORMATION FOR SEQ ID NO:2:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown -continued ( x i ) SEQUENCE DESCRIPTION: SEQ ID NO:2:

GCATCTGACC GTGCAATCGA AGGTCGTTGA GGGATCC 37

( 2 ) INFORMATION FOR SEQ ID NO:3:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:3:

GACGCTGACC GTGCAATCGAAG GTCGTTGA GGGATCC 37

( 2 ) INFORMATION FOR SEQ ID NO:4:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:4:

GACTCTGCAC GTGCAATCGAAG GTCGTTGA GGGATCC 37

( 2 ) INFORMATION FOR SEQ ID NO:5:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:5:

GACTCTGACG CTGCAATCGA AGGTCGTTGA GGGATCC 37

( 2 ) INFORMATION FOR SEQ ID NO:6:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:6:

GACTCTGACC GTTCCATCGA AGGTCGTTGA GGGATCC 37

( 2 ) INFORMATION FOR SEQ ID NO:7:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:7:

GACTCTGACC GTGCAGCTGA AGGTCGTTGA GGGATCC 37

( 2 ) INFORMATION FOR SEQ ID NO:8:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:8:

GACTCTGACC GTGCAATCGC TGGTCGTTGA GGGATCC 37

( 2 ) INFORMATION FOR SEQ ID NO:9:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:9:

GACTCTGACC GTGCAATCGA AGCACGTTGA GGGATCC 37

( 2 ) INFORMATION FOR SEQ ID NO:10:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:10:

GACTCTGACC GTGCAATCGA AGGCGCATGA GGGATCC 37

( 2 ) INFORMATION FOR SEQ ID NO:11:

( i ) SEQUENCE CHARACTERISTICS:
( A ) LENGTH: 141 amino acids
( B ) TYPE: amino acid
( C ) STRANDEDNESS: unknown
( D ) TOPOLOGY: unknown ( x i ) SEQUENCE DESCRIPTION: SEQ ID NO:11:

Lys Leu Met Lys Lys Ile Pro Gln Ile Ser Asp Ala Glu Leu Glu Val
1 5 10 15

Met Lys Val Ile Trp Lys His Ser Ser Ile Asn Thr Asn Glu Val Ile
20 25 30

Lys Glu Leu Ser Lys Thr Ser Thr Trp Ser Pro Lys Thr Ile Gln Thr
35 40 45

Met Leu Leu Arg Leu Ile Lys Lys Gly Ala Leu Asn His His Lys Glu
50 55 60

Gly Arg Val Phe Val Tyr Thr Pro Asn Ile Asp Glu Ser Asp Tyr Ile
65 70 75 80

Glu Val Lys Ser His Ser Phe Leu Asn Arg Phe Tyr Asn Gly Thr Leu
85 90 95

Asn Ser Met Val Leu Asn Phe Leu Glu Asn Asp Gln Leu Ser Gly Glu
100 105 110

Glu Ile Asn Glu Leu Tyr Gln Ile Leu Glu Glu His Lys Asn Arg Lys
115 120 125

Lys Glu Pro Trp Asp Ser Asp Arg Ala Ile Glu Gly Arg
130 135 140

( 2 ) INFORMATION FOR SEQ ID NO:12:

( i ) SEQUENCE CHARACTERISTICS:
( A ) LENGTH: 9 amino acids
( B ) TYPE: amino acid
( C ) STRANDEDNESS: unknown
( D ) TOPOLOGY: unknown ( x i ) SEQUENCE DESCRIPTION: SEQ ID NO:12:

Ala Ser Asp Arg Ala Ile Glu Gly Arg
1 5

( 2 ) INFORMATION FOR SEQ ID NO:13:

( i ) SEQUENCE CHARACTERISTICS:
( A ) LENGTH: 9 amino acids
( B ) TYPE: amino acid
( C ) STRANDEDNESS: unknown
( D ) TOPOLOGY: unknown ( x i ) SEQUENCE DESCRIPTION: SEQ ID NO:13:

Asp Ala Asp Arg Ala Ile Glu Gly Arg
1 5

( 2 ) INFORMATION FOR SEQ ID NO:14:

( i ) SEQUENCE CHARACTERISTICS:
( A ) LENGTH: 9 amino acids
( B ) TYPE: amino acid
( C ) STRANDEDNESS: unknown
( D ) TOPOLOGY: unknown ( x i ) SEQUENCE DESCRIPTION: SEQ ID NO:14:

Asp Ser Ala Arg Ala Ile Glu Gly Arg
1 5

( 2 ) INFORMATION FOR SEQ ID NO:15:

( i ) SEQUENCE CHARACTERISTICS:
( A ) LENGTH: 9 amino acids
( B ) TYPE: amino acid
( C ) STRANDEDNESS: unknown
( D ) TOPOLOGY: unknown ( x i ) SEQUENCE DESCRIPTION: SEQ ID NO:15:

Asp Ser Asp Ala Ala Ile Glu Gly Arg
1 5

( 2 ) INFORMATION FOR SEQ ID NO:16:

( i ) SEQUENCE CHARACTERISTICS:
( A ) LENGTH: 9 amino acids
( B ) TYPE: amino acid
( C ) STRANDEDNESS: unknown
( D ) TOPOLOGY: unknown ( x i ) SEQUENCE DESCRIPTION: SEQ ID NO:16:

Asp Ser Asp Arg Ser Ile Glu Gly Arg
1 5

( 2 ) INFORMATION FOR SEQ ID NO:17:

( i ) SEQUENCE CHARACTERISTICS:
( A ) LENGTH: 9 amino acids
( B ) TYPE: amino acid
( C ) STRANDEDNESS: unknown
( D ) TOPOLOGY: unknown ( x i ) SEQUENCE DESCRIPTION: SEQ ID NO:17:

Asp Ser Asp Arg Ala Ala Glu Gly Arg
1 5

( 2 ) INFORMATION FOR SEQ ID NO:18:

( i ) SEQUENCE CHARACTERISTICS:
( A ) LENGTH: 9 amino acids
( B ) TYPE: amino acid
( C ) STRANDEDNESS: unknown
( D ) TOPOLOGY: unknown ( x i ) SEQUENCE DESCRIPTION: SEQ ID NO:18:

-continued

Asp Ser Asp Arg Ala Ile Ala Gly Arg
1 5

( 2 ) INFORMATION FOR SEQ ID NO:19:

( i ) SEQUENCE CHARACTERISTICS:
( A ) LENGTH: 9 amino acids
( B ) TYPE: amino acid
( C ) STRANDEDNESS: unknown
( D ) TOPOLOGY: unknown ( x i ) SEQUENCE DESCRIPTION: SEQ ID NO:19:

Asp Ser Asp Arg Ala Ile Glu Ala Arg
1 5

( 2 ) INFORMATION FOR SEQ ID NO:20:

( i ) SEQUENCE CHARACTERISTICS:
( A ) LENGTH: 9 amino acids
( B ) TYPE: amino acid
( C ) STRANDEDNESS: unknown
( D ) TOPOLOGY: unknown ( x i ) SEQUENCE DESCRIPTION: SEQ ID NO:20:

Asp Ser Asp Arg Ala Ile Glu Gly Ala
1 5

( 2 ) INFORMATION FOR SEQ ID NO:21:

( i ) SEQUENCE CHARACTERISTICS:
( A ) LENGTH: 24 base pairs
( B ) TYPE: nucleic acid
( C ) STRANDEDNESS: unknown
( D ) TOPOLOGY: unknown ( x i ) SEQUENCE DESCRIPTION: SEQ ID NO:21:

GGAAGCTTAT GAAAAAAATA CCTC 24

( 2 ) INFORMATION FOR SEQ ID NO:22:

( i ) SEQUENCE CHARACTERISTICS:
( A ) LENGTH: 34 base pairs
( B ) TYPE: nucleic acid
( C ) STRANDEDNESS: unknown
( D ) TOPOLOGY: unknown ( x i ) SEQUENCE DESCRIPTION: SEQ ID NO:22:

GGGGATCCCT CACCATGGTT CCTTCTTTCT GTTC 34

( 2 ) INFORMATION FOR SEQ ID NO:23:

( i ) SEQUENCE CHARACTERISTICS:
( A ) LENGTH: 11 base pairs
( B ) TYPE: nucleic acid
( C ) STRANDEDNESS: unknown
( D ) TOPOLOGY: unknown ( x i ) SEQUENCE DESCRIPTION: SEQ ID NO:23:

ATCGAGGTAG G 11

( 2 ) INFORMATION FOR SEQ ID NO:24:

( i ) SEQUENCE CHARACTERISTICS:
( A ) LENGTH: 24 base pairs
( B ) TYPE: nucleic acid
( C ) STRANDEDNESS: unknown
( D ) TOPOLOGY: unknown -continued ( x i ) SEQUENCE DESCRIPTION: SEQ ID NO:24:

GGAAGCTTAT GAAAAAAATA CCTC 24

( 2 ) INFORMATION FOR SEQ ID NO:25:

( i ) SEQUENCE CHARACTERISTICS:
( A ) LENGTH: 34 base pairs
( B ) TYPE: nucleic acid
( C ) STRANDEDNESS: unknown
( D ) TOPOLOGY: unknown ( x i ) SEQUENCE DESCRIPTION: SEQ ID NO:25:

GGGGATCCCT CACCATGGTT CCTTCTTTCT GTTC 34

( 2 ) INFORMATION FOR SEQ ID NO:26:

( i ) SEQUENCE CHARACTERISTICS:
( A ) LENGTH: 47 base pairs
( B ) TYPE: nucleic acid
( C ) STRANDEDNESS: unknown
( D ) TOPOLOGY: unknown ( x i ) SEQUENCE DESCRIPTION: SEQ ID NO:26:

CATGGGACTC TGACCGTGCA ATCGAAGGTC GTTGAGGGAT CCGGTAC 47

( 2 ) INFORMATION FOR SEQ ID NO:27:

( i ) SEQUENCE CHARACTERISTICS:
( A ) LENGTH: 39 base pairs
( B ) TYPE: nucleic acid
( C ) STRANDEDNESS: unknown
( D ) TOPOLOGY: unknown ( x i ) SEQUENCE DESCRIPTION: SEQ ID NO:27:

CGGATCCCTC AACGACCTTC GATTGCACGG TCAGAGTCC 39

( 2 ) INFORMATION FOR SEQ ID NO:28:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:28:

CATGGGCATC TGACCGTGCA ATCGAAGGTC GTTGAGG 37

( 2 ) INFORMATION FOR SEQ ID NO:29:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:29:

GATCCCTCAA CGACCTTCGA TTGCACGGTC AGATGCC 37

( 2 ) INFORMATION FOR SEQ ID NO:30:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:30:

-continued

CATGGGACGC TGACCGTGCA ATCGAAGGTC GTTGAGG 37

( 2 ) INFORMATION FOR SEQ ID NO:31:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:31:

GATCCCTCAA CGACCTTCGA TTGCACGGTC AGCGTCC 37

( 2 ) INFORMATION FOR SEQ ID NO:32:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:32:

CATGGGACTC TGCACGTGCA ATCGAAGGTC GTTGAGG 37

( 2 ) INFORMATION FOR SEQ ID NO:33:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:33:

GATCCCTCAA CGACCTTCGA TTGCACGTGC AGAGTCC 37

( 2 ) INFORMATION FOR SEQ ID NO:34:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:34:

CATGGGACTC TGACGCTGCA ATCGAAGGTC GTTGAGG 37

( 2 ) INFORMATION FOR SEQ ID NO:35:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:35:

GATCCCTCAA CGACCTTCGA TTGCAGCGTC AGAGTCC 37

( 2 ) INFORMATION FOR SEQ ID NO:36:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:36:

CATGGGACTC TGACCGTTCC ATCGAAGGTC GTTGAGG 37

-continued ( 2 ) INFORMATION FOR SEQ ID NO:37:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:37:

GATCCCTCAA CGACCTTCGA TGGAACGGTC AGAGTCC 37

( 2 ) INFORMATION FOR SEQ ID NO:38:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:38:

CATGGGACTC TGACCGTGCA GCTGAAGGTC GTTGAGG 37

( 2 ) INFORMATION FOR SEQ ID NO:39:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:39:

GATCCCTCAA CGACCTTCAG CTGCACGGTC AGAGTCC 37

( 2 ) INFORMATION FOR SEQ ID NO:40:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:40:

CATGGGACTC TGACCGTGCA ATCGCTGGTC GTTGAGG 37

( 2 ) INFORMATION FOR SEQ ID NO:41:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:41:

GATCCCTCAA CGACCAGCGA TTGCACGGTC AGAGTCC 37

( 2 ) INFORMATION FOR SEQ ID NO:42:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:42:

CATGGGACTC TGACCGTGCA ATCGAAGCAC GTTGAGG 37

( 2 ) INFORMATION FOR SEQ ID NO:43:

-continued ( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:43:

GATCCCTCAA CGTGCTTCGAT TGCACGGTCA GAGTCC 37

( 2 ) INFORMATION FOR SEQ ID NO:44:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:44:

CATGGGACTC TGACCGTGCA ATCGAAGGCG CATGAGG 37

( 2 ) INFORMATION FOR SEQ ID NO:45:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:45:

GATCCCTCAT GCGCCTTCGA TTGCACGGTC AGAGTCC 37

( 2 ) INFORMATION FOR SEQ ID NO:46:

( i ) SEQUENCE CHARACTERISTICS:
( A ) LENGTH: 43 base pairs
( B ) TYPE: nucleic acid
( C ) STRANDEDNESS: unknown
( D ) TOPOLOGY: unknown ( x i ) SEQUENCE DESCRIPTION: SEQ ID NO:46:

GGGGCCATGG ATCGAAGGTC GTACTAGTCG CGCTTATGCC ACG 43

( 2 ) INFORMATION FOR SEQ ID NO:47:

( i ) SEQUENCE CHARACTERISTICS:
( A ) LENGTH: 34 base pairs
( B ) TYPE: nucleic acid
( C ) STRANDEDNESS: unknown
( D ) TOPOLOGY: unknown ( x i ) SEQUENCE DESCRIPTION: SEQ ID NO:47:

CCCCGGATCC TCACAGCTCT TGCTTTGCAA TCGT 34

( 2 ) INFORMATION FOR SEQ ID NO:48:

( i ) SEQUENCE CHARACTERISTICS:
( A ) LENGTH: 32 base pairs
( B ) TYPE: nucleic acid
( C ) STRANDEDNESS: unknown
( D ) TOPOLOGY: unknown ( x i ) SEQUENCE DESCRIPTION: SEQ ID NO:48:

GAGAGAAAGC TTATGAAAAA AATACCTCAA AT 32

( 2 ) INFORMATION FOR SEQ ID NO:49:

( i ) SEQUENCE CHARACTERISTICS:

-continued ( A ) LENGTH: 65 base pairs
( B ) TYPE: nucleic acid
( C ) STRANDEDNESS: unknown
( D ) TOPOLOGY: unknown ( x i ) SEQUENCE DESCRIPTION: SEQ ID NO:49:

GGAGCCGCCA CCACCGCTGC CACCACCGCC AGAACCGCCG CCACCTTCCT TCTTTCTGTT 60

CTTAT 65

( 2 ) INFORMATION FOR SEQ ID NO:50:

( i ) SEQUENCE CHARACTERISTICS:
( A ) LENGTH: 68 base pairs
( B ) TYPE: nucleic acid
( C ) STRANDEDNESS: unknown
( D ) TOPOLOGY: unknown ( x i ) SEQUENCE DESCRIPTION: SEQ ID NO:50:

GGTGGCGGCG GTTCTGGCGG TGGTGGCAGC GGTGGTGGCG GCTCCTGGTG GTATCACGGA 60

AAACTTGA 68

( 2 ) INFORMATION FOR SEQ ID NO:51:

( i ) SEQUENCE CHARACTERISTICS:
( A ) LENGTH: 38 base pairs
( B ) TYPE: nucleic acid
( C ) STRANDEDNESS: unknown
( D ) TOPOLOGY: unknown ( x i ) SEQUENCE DESCRIPTION: SEQ ID NO:51:

CCTTCCGGAT CCTCATCAAA CTGGGTAAAG TAATTTTT 38

( 2 ) INFORMATION FOR SEQ ID NO:52:

( i ) SEQUENCE CHARACTERISTICS:
( A ) LENGTH: 72 base pairs
( B ) TYPE: nucleic acid
( C ) STRANDEDNESS: single
( D ) TOPOLOGY: linear ( x i ) SEQUENCE DESCRIPTION: SEQ ID NO:52:

CATGGATCGA AGGTCGTATC AGCCAGGCTG TTCACGCAGC TCACGCAGAA ATCAACGAAG 60

CTGGTCGTTG AG 72

( 2 ) INFORMATION FOR SEQ ID NO:53:

( i ) SEQUENCE CHARACTERISTICS:
( A ) LENGTH: 72 base pairs
( B ) TYPE: nucleic acid
( C ) STRANDEDNESS: single
( D ) TOPOLOGY: linear ( x i ) SEQUENCE DESCRIPTION: SEQ ID NO:53:

GATCCTCAAC GACCAGCTTC GTTGATTTCT GCGTGAGCTG CGTGAACAGC CTGGCTGATA 60

CGACCTTCGA TC 72

( 2 ) INFORMATION FOR SEQ ID NO:54:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( x i ) SEQUENCE DESCRIPTION: SEQ ID NO:54:

-continued

```
Ile Glu Gly Arg Ile Ser Gln Ala Val His Ala Ala His Ala Glu Ile
1               5                   10                  15

Asn Glu Ala Gly Arg
            20
```

( 2 ) INFORMATION FOR SEQ ID NO:55:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( x i ) SEQUENCE DESCRIPTION: SEQ ID NO:55:

```
Ile Glu Gly Arg Asn Leu Cys Asn Ile Pro Cys Ser Ala Leu Leu Ser
1               5                   10                  15

Ser
```

( 2 ) INFORMATION FOR SEQ ID NO:56:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( x i ) SEQUENCE DESCRIPTION: SEQ ID NO:56:

```
CATGGATCGA AGGTCGTAAC CTATGCAACA TCCCGTGCAG CGCACTGCTG AGCAGCTGAG     60
```

( 2 ) INFORMATION FOR SEQ ID NO:57:

( i ) SEQUENCE CHARACTERISTICS:
( A ) LENGTH: 53 base pairs
( B ) TYPE: nucleic acid
( C ) STRANDEDNESS: single
( D ) TOPOLOGY: linear ( x i ) SEQUENCE DESCRIPTION: SEQ ID NO:57:

```
GATCCTCAGC TGCTCAGCAG TGCGCTGCAC GGGATGCATA GGTTACGACC TTC     53
```